US006941171B2

(12) United States Patent
Mann et al.

(10) Patent No.: US 6,941,171 B2
(45) Date of Patent: Sep. 6, 2005

(54) IMPLANTABLE STIMULATOR METHODS FOR TREATMENT OF INCONTINENCE AND PAIN

(75) Inventors: Carla M. Mann, Los Angeles, CA (US); Todd K. Whitehurst, Sherman Oaks, CA (US); James P. McGivern, Stevenson Ranch, CA (US); Gerald E. Loeb, So. Pasadena, CA (US); Frances J. R. Richmond, So. Pasadena, CA (US)

(73) Assignee: Advanced Bionics Corporation, Valencia, CA (US)

( * ) Notice: Subject to any disclaimer, the term of this patent is extended or adjusted under 35 U.S.C. 154(b) by 300 days.

(21) Appl. No.: 09/931,804

(22) Filed: Aug. 16, 2001

(65) Prior Publication Data

US 2002/0055761 A1 May 9, 2002

Related U.S. Application Data

(63) Continuation-in-part of application No. 09/642,979, filed on Aug. 18, 2000, now Pat. No. 6,735,474, which is a continuation-in-part of application No. PCT/US99/14775, filed on Jun. 29, 1999.
(60) Provisional application No. 60/173,054, filed on Dec. 24, 1999, and provisional application No. 60/091,762, filed on Jul. 6, 1998.

(51) Int. Cl.[7] ............................................. A61N 1/36
(52) U.S. Cl. .............................. 607/39; 607/41; 607/3; 128/898; 604/891.1
(58) Field of Search .................. 607/3, 39, 41, 607/45, 116, 118, 138, 40, 46, 143, 62, 30; 604/890.1, 891.1, 21; 128/898

(56) References Cited

U.S. PATENT DOCUMENTS 3,628,538 A * 12/1971 Vincent et al. ............... 607/62

| 3,646,940 A | 3/1972 | Timm et al. |
| 3,650,276 A | 3/1972 | Burghele et al. |

(Continued)

FOREIGN PATENT DOCUMENTS

| EP | 245547 B1 | 8/1990 |
| WO | WO-97/18857 A1 | 5/1997 |
| WO | WO-98/37926 A1 | 9/1998 |

(Continued)

OTHER PUBLICATIONS

McGuire, et al., "Treatment of Motor and Sensory Detrusor Instability by Electrical Stimulation", Journal of Urology, vol. 129, No. 1, (1983), pp. 78–79.

(Continued)

*Primary Examiner*—Kennedy Schaetzle
(74) *Attorney, Agent, or Firm*—Laura Haburay Bishop; Bryant R. Gold

(57) ABSTRACT

A method and system for treatment of incontinence, urgency, frequency, and/or pelvic pain includes implantation of electrodes on a lead or the discharge portion of a catheter adjacent the perineal nerve(s) or tissue(s) to be stimulated. Stimulation pulses, either electrical or drug infusion pulses, are supplied by a stimulator implanted remotely, and through the lead or catheter, which is tunneled subcutaneously between the stimulator and stimulation site. For instance, the system and method reduce or eliminate the incidence of unintentional episodes of bladder emptying by stimulating nerve pathways that diminish involuntary bladder contractions, improve closure of the bladder outlet, and/or improve the long-term health of the urinary system by increasing bladder capacity and period between emptying. Moreover, the system and method allow a patient to be taught to receive one or more patterns of neural stimulation that can be prescribed by a physician and administered without continuous oversight by a clinical practitioner.

21 Claims, 8 Drawing Sheets

U.S. PATENT DOCUMENTS

| | | | |
|---|---|---|---|
| 3,667,477 A | | 6/1972 | Susset et al. |
| 3,870,051 A | | 3/1975 | Brindley |
| 4,387,719 A | | 6/1983 | Plevnik et al. |
| 4,406,288 A | | 9/1983 | Horwinski et al. |
| 4,431,001 A | | 2/1984 | Hakansson et al. |
| 4,569,351 A | | 2/1986 | Tang |
| 4,585,005 A | | 4/1986 | Lue et al. |
| 4,607,639 A | | 8/1986 | Tanagho et al. |
| 4,703,755 A | | 11/1987 | Tanagho et al. |
| 4,739,764 A | | 4/1988 | Lue et al. |
| 4,771,779 A | | 9/1988 | Tanagho et al. |
| 5,094,242 A | | 3/1992 | Gleason et al. |
| 5,193,539 A | | 3/1993 | Schulman et al. |
| 5,193,540 A | | 3/1993 | Schulman et al. |
| 5,199,430 A | | 4/1993 | Fang et al. |
| 5,291,902 A | * | 3/1994 | Carman ............ 607/138 |
| 5,312,439 A | | 5/1994 | Loeb |
| 5,324,316 A | | 6/1994 | Schulman et al. |
| 5,358,514 A | | 10/1994 | Schulman et al. |
| 5,405,367 A | | 4/1995 | Schulman et al. |
| 5,562,717 A | * | 10/1996 | Tippey et al. .......... 607/41 |
| 5,571,148 A | | 11/1996 | Loeb et al. |
| 5,702,428 A | | 12/1997 | Tippey et al. |
| 5,833,595 A | * | 11/1998 | Lin ................ 600/29 |
| 5,957,965 A | | 9/1999 | Moumane et al. |
| 5,984,854 A | | 11/1999 | Ishikawa et al. |
| 6,026,326 A | | 2/2000 | Bardy |
| 6,051,017 A | | 4/2000 | Loeb et al. |
| 6,061,596 A | | 5/2000 | Richmond et al. |
| 6,104,955 A | | 8/2000 | Bourgeois |
| 6,104,960 A | | 8/2000 | Duysens et al. |
| 6,185,452 B1 | | 2/2001 | Schulman et al. |
| 6,208,894 B1 | | 3/2001 | Schulman et al. |
| 6,240,316 B1 | | 5/2001 | Richmond et al. |
| 6,266,557 B1 | * | 7/2001 | Roe et al. ............ 600/546 |
| 6,360,750 B1 | | 3/2002 | Gerber et al. |
| 6,366,814 B1 | * | 4/2002 | Boveja et al. .......... 607/45 |
| 6,407,308 B1 | | 6/2002 | Roe et al. |
| 6,650,943 B1 | * | 11/2003 | Whitehurst et al. ........ 607/39 |
| 6,659,936 B1 | * | 12/2003 | Furness et al. ........ 600/30 |
| 2001/0002441 A1 | | 5/2001 | Boveja |

FOREIGN PATENT DOCUMENTS

| | | |
|---|---|---|
| WO | WO-98/43700 A1 | 10/1998 |
| WO | WO-98/43701 A1 | 10/1998 |
| WO | WO-00/01320 A3 | 1/2000 |
| WO | WO-00/19939 A1 | 4/2000 |
| WO | WO-00/25859 A1 | 5/2000 |
| WO | WO-01/52729 A2 | 7/2001 |
| WO | WO-01/54767 A1 | 8/2001 |
| WO | WO-01/60445 A2 | 8/2001 |
| WO | WO-02/20086 A1 | 3/2002 |

OTHER PUBLICATIONS

Murray, Letter Re: "Treatment of Motor and Sensory Detrusor Instability by Electrical Stimulation" and Re: "The Neurophysiological Basis of Bladder Inyhibition in Response to Intravaginal Electrical Stimulation", Journal of Urology, vol. 131, No. 2, (1984), p. 356.

Crocker, et al., "Transcutaneous Electrical Nerve Stimulation in Urinary Retention", Southern Medical Journal, vol. 78, No. 12, (1985), pp. 1515–1516.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781–790.

Shealy, et al., "Electrical Inhibition of Pain by Stimulation of the Dorsal Column", Anesthesia and Analgesia, vol. 46, (1967), pp. 489–491.

Vodusek, et al., "Detrusor Inhibition Induced by Stimulation of Pudendal Nerve Afferents", Neurourology and Urodynamics, vol. 5, (1986), pp. 381–389.

Vodusek, et al., "Detrusor Inhibition on Selective Pudendal Nerve Stimulation in the Perineum", Neurourology and Urodynamics, vol. 6, (1988), pp. 389–393.

Sundin, et al., "Detrusor Inhibition Induced from Mechanical Stimulation of the Anal Region and From Electrical Stimulation of Pudendal Nerve Afferents", Investigative Urology, vol. 11, No. 5, (1974), pp. 374–378.

Ohlsson, et al., "Effects of External and Direct Pudendal Nerve Maximal Electrical Stimulation in the Treatment of the Uninhibited Overactive Bladder", British Journal of Urology, vol. 64, (1989), pp. 374–380.

Fall, et al., "Electrical Stimulation. A Physilogic Approach to the Treatment of Urinary Incontinence", Urol Clin North Am, vol. 18, No. 2 (May 1991), pp. 393–407.

Malouf, et al., "Permanent Sacral Nerve Stimulation for Fecal Incontinence", Ann Surg. vol. 232, No. 1, (Jul. 2000), pp. 143–148.

Schmidt, et al., "Sacral Nerve Stimulation for Treatment of Refractory Urinary Urge Incontinence, Sacral Nerve Stimulation Study Group", J Urol, vol. 162, No. 2, (Aug. 1999), pp. 352–357.

Shaker, et al., "Sacral Nerve Root Neuromodulation: an Effective Treatment for Refractory Urge Incontinence", J Urol, vol. 159, No. 5, (May 1998), pp. 1516–1519.

Shafik, et al., "Sacral Root Stimulation for Controlled Defecation", Eur Surg Res, vol. 27, No. 1 (1995), pp. 63–68.

Teague, et al., "Electric Pelvic Floor Stimulation. Mechanism of Action." Invest Urol, vol. 15, No. 1 (Jul. 1977), pp. 65–69.

Merrill, "The Treatment of Detrusor Incontinence by Electrical Stimulation", J Urol, vol. 122, No. 4, (Oct. 1979), pp. 515–517.

Merrill, et al., "Urinary Incontinence. Treatment with Electrical Stimulation of the Pelvic Floor", Urology, vol. 5, No. 1, (Jan. 1975), pp. 67–72.

Sawan, et al., "Computerized Transcutaneous Control of a Multichannel Implantable Urinary Prosthesis", IEEE Transactions on Biomedical Engineering, vol. 39, No. 6, (Jun. 1, 1992), pp. 600–609.

UroSurge—SANS 2; printed Mar. 2, 2000; pp. 1–2.

UroSurge—SANS (Stoller Afferent Nerve Stimulation) Device; printed Mar. 2, 2000; pp. 1–5.

UroSurge—SANS AUA Abstract; printed Mar. 2, 2000; pp. 1–2.

IC in the News! ICN Feature Stories; printed Mar. 2, 2000; pp. 1–7.

What is Medtronic InterStim Therapy for Urinary Control; printed Mar. 2, 2000; pp. 1–2.

Medtronic's InterStim Therapy for Urinary Co . . . : For People with Bladder Control Problem; printed Mar. 2, 2000; pp. 1–2.

Medtronic's InterStim Therapy for Urinary Control: For Health Care Professionals; printed Mar. 2, 2000; pp. 1–2.

Medtronic InterStim Urinary Control—FAQ's; printed Mar. 2, 2000; pp. 1–7.

Our Products: Incontinence Therapies: Innova® PFS; printed Mar. 2, 2000; pp. 1–2.

Our Products: Incontinence Therapies; printed Mar. 2, 2000; pp. 1–2.

Lower Back Pain, Neck Pain, Arthritis—Pain Management & Muscle Stimulation—Ottawa . . . ; printed Mar. 2, 2000; p. 1.

Whitehurst, McGivern, and Mann inventors for AB–125U; U.S. Appl. No. 09/929,596; filed Aug. 13, 2001; entitled "Fully Implantable Neurostimulator for Autonomic Nerve Fiber Stimulation as a Therapy for Urinary and Bowel Dysfunction".

Whitehurst, McGivern, Mann, and Kuzma inventors for AB–126U; U.S. Appl. No. 09/929,597; filed Aug. 13, 2001; entitled "Fully Implantable Microstimulator for Spinal Nerve, Spinal Nerve Root, and/or Spinal Cord Stimulation as a Therapy for Chronic Pain".

* cited by examiner

IMPLANTABLE STIMULATOR METHODS FOR TREATMENT OF INCONTINENCE AND PAIN

This application is a continuation-in-part (CIP) of copending U.S. patent application Ser. No. 09/642,979, filed 18 Aug. 2000, now U.S. Pat. No. 6,735,474 which in turn is a CIP of PCT patent application Ser. No. PCT/US99/14775, filed 29 Jun. 1999, which in turn claims priority to, and the benefit of, prior U.S. patent application Ser. No. 60/091,762, filed 6 Jul. 1998. U.S. patent application Ser. No. 09/642,979 also claims the benefit of U.S. patent application Ser. No. 60/173,054, filed 24 Dec. 1999. The above-listed applications are incorporated herein by reference.

FIELD OF THE INVENTION

The present invention relates to implantable stimulator systems, and more particularly to an implantable stimulator system utilizing one or more implantable stimulators for treating incontinence and/or pain.

BACKGROUND OF THE INVENTION

Urinary incontinence is a clinical condition characterized by failure to hold urine in the bladder under normal conditions of pressure and filling. Urinary incontinence afflicts an estimated 13 million Americans. A 1980 British postal survey of 22,430 people showed a prevalence of urinary incontinence of 8.5% in women and 1.6% in men aged 15–64, and 11.6% in women and 6.9% in men aged 65 and over.

Six of every seven adult incontinence cases occur in women; 15% to 30% of women experience incontinence during their lifetimes. Women are more at risk than men because of pelvic nerve trauma during childbirth and the comparative shortness of the female urethra (around two inches versus ten in men). Women who have their first child when over age 30 or who use the drug oxytocin for inducing labor appear to be at increased risk for urinary incontinence later on. (Such medically-induced labor tends to subject pelvic muscles and nerves to greater forces than does natural labor.) In addition, women who perform high-impact exercise, such as gymnasts, and softball, volleyball, and basketball players, are susceptible to urinary leakage, particularly those with a low foot arch, which, on impact, increases the shock to the pelvic area. In addition, a study of 600 women found that smokers and former smokers are twice as likely to develop incontinence than are women who never smoked. According to one 1999 study, urge incontinence is more common among older postmenopausal women who are diabetic or who reported two urinary tract infections within the past year. Obesity is also a major factor for incontinence in older women.

Forms of Urinary Incontinence

The most common forms of urinary incontinence can arise from either a failure of muscles around the bladder neck and urethra to maintain closure of the urinary outlet (so-called stress incontinence) or from abnormally heightened commands from the spinal cord to the bladder that produce unanticipated bladder contractions (so-called urge incontinence). Patients with stress incontinence experience minor leakage from activities that apply pressure to a full bladder, such as coughing, sneezing, laughing, running, lifting, or even standing. People with urge incontinence (also called hyperactive or irritable bladder) need to urinate frequently or are unable to reach the bathroom before leakage. When the bladder reaches capacity, the nerves appropriately signal the brain that the bladder is full, but the urge to void cannot be voluntarily suppressed—even temporarily. In a variant type of urge incontinence called reflex incontinence, the sensation of fullness is not adequately communicated to the brain, and in the absence of the brain's inhibition of this automatic process, the bladder releases urine.

Another common form of the disorder is overflow incontinence, which results when the bladder cannot empty completely, generally because of a partial obstruction or an inactive bladder muscle. In contrast to urge incontinence, the bladder is less active than normal. It cannot empty properly and so becomes distended. Eventually this distention stretches the internal sphincter until it opens partially and leakage occurs. Functional, or environmental, incontinence encompasses a variety of conditions in which the patient is unable to use the bathroom because of physical or emotional impairments. Approximately 40% of incontinence patients fall into more than one of these four categories (stress, urge, overflow, and functional incontinence), and experience so-called mixed incontinence.

Anatomy and Physiology of the Lower Urinary Tract

The urinary bladder is composed of smooth muscle collectively referred to as the detrusor muscle. Smooth muscle of the urethra is contiguous with the detrusor muscle and is referred to as the internal urethral sphincter, although it is not a true anatomic sphincter. Skeletal muscle surrounding the urethra is called the external urethral sphincter.

Innervation of the lower urinary tract is complex. Tight junctions between bladder smooth muscle cells allow for transmission of nerve impulses from cell to cell. The hypogastric nerve, originating from spinal cord segments of L1 through L4, supplies sympathetic innervation to the bladder and urethra. The pelvic nerve, originating from the spinal cord segments S1 through S3, supplies parasympathetic (cholinergic) innervation to the detrusor muscle and transmits sensory impulses from the bladder. Somatic innervation of the muscle of the external urethral sphincter is distributed via the pudendal nerve, originating from spinal cord segments S1 through S3. The pudendal nerve also innervates muscles of the anal sphincter and perineal region, and it also transmits sensation from the perineal region and the urethral and anal sphincters.

The sympathetic and somatic nervous systems dominate the storage phase of micturition. Sympathetic stimulation of beta-adrenergic receptors in the detrusor muscle results in bladder relaxation to accommodate filling. Sympathetic stimulation of alpha-adrenergic receptors in the neck of the bladder and internal urethral sphincter maintains continence. Sympathetic pathways also inhibit parasympathetic bladder innervation during storage. Stimulation of the pudendal nerve results in increased tone of the external urethral sphincter, contributing to continence. When the bladder is full, sensation is transmitted via the pelvic nerve to the sacral spinal cord, and subsequently the brainstem. Voluntary control of urination originates from the cerebral cortex. The storage phase of the urinary bladder can be switched to the voiding phase either voluntarily or involuntarily (reflexively).

Signals to the cortical center generally occur when bladder volume has reached 250 mL to 300 mL. When urination is desired, neural impulses from the cortex are transmitted through the spinal cord and pelvic nerves to the detrusor muscle. Daytime emptying of the bladder may occur as often as every few hours or as infrequently as every 8 to 12 hours. During the emptying phase of micturition, parasympathetic (cholinergic) activity of the pelvic nerves causes the detrusor muscle to contract and the bladder to empty. Simultaneous inhibition of sympathetic and somatic stimulation of the urethral smooth and skeletal muscle results in urethral relaxation. Following complete emptying of the bladder or voluntary cessation of urination, the storage phase begins again. External urethral sphincter tone can increase in response to sudden increases in abdominal pressure (e.g., during coughing) to maintain continence. Disruption of tight junctions, peripheral nerves, spinal cord segments, or higher brain centers may alter micturition.

Reflex Arcs in the Lower Urinary Tract

The function of the lower urinary tract is modulated by several reflex arcs. The most prominent of these is a positive feedback reflex that modulates micturition. Mechanoreceptors in the bladder are distended when the bladder is at capacity, and they trigger a coordinated micturition reflex via a center in the upper pons and perhaps through a spinal reflex as well. The bladder contracts, causing an even greater distention of the mechanoreceptors, leading to even greater activation of the micturition reflex and bladder contraction. This ensures that the bladder is completely emptied during normal voiding.

Other lower urinary tract reflexes are inhibitory. The external urethral sphincter is reflexively activated by mechanoreceptors during bladder filling, so that sphincter pressure increases as needed. Anal dilatation has been demonstrated to reflexively inhibit detrusor contraction, thereby preventing involuntary urine leakage during defecation. Gentle mechanical stimulation of the genital and perineal regions also reflexively inhibits detrusor contraction, thereby preventing involuntary urine leakage during sexual stimulation and coitus. The afferent portions of these reflex arcs are carried by the pudendal nerve, which carries somatic sensory information from the pelvic floor, and the pelvic nerve, which carries much of the pelvic visceral sensations. Bladder contraction is also reflexively inhibited by the activation of stretch fibers in pelvic and limb muscles, thereby preventing involuntary urine leakage during physical activity.

Neurologic Causes of Incontinence

Urinary incontinence may be associated with neurologic disease. Neurologic abnormalities may disrupt the detrusor muscle, urethral sphincters, or both. Neurologic incontinence may result from trauma, tumors, or herniated intervertebral discs. The location of the lesion will dictate the type of micturition disorder and other concurrent neurologic abnormalities.

Patients with upper motor neuron (UMN) lesions—those above the sacral spinal cord segments—lack voluntary control of micturition. Urination may be initiated by spinal reflexes, but an absence of sensation and central nervous system control, and the failure of the sphincters to relax, leads to interrupted, involuntary, and/or incomplete voiding. Manual bladder expression is difficult if sphincter hypertonia is present, but the urethra can be catheterized normally. Overflow of urine occurs when the bladder pressure exceeds sphincter resistance. The perineal reflex is intact.

Detrusor instability (a.k.a. detrusor areflexia) with decreased sphincter tone results from disease of sacral spinal cord segments or bilateral lesions of the sacral spinal nerve roots (i.e., lower motor neuron, or LMN, lesions). Voluntary control of urination is absent. Fecal incontinence may also be present, and perineal reflexes may be absent. Detrusor instability may also occur secondary to prolonged overdistention of the bladder. Tight junctions between muscle cells are disrupted, preventing spread of nerve impulses. The patient will attempt to void because sensory pathways are intact, but the atonic, flaccid bladder is unable to contract. Residual urine volume is large.

Reflex dyssynergia occurs with incomplete spinal cord lesions cranial to the sacral spinal cord segments. The detrusor reflex is normal to hyperactive, and the urethral sphincters are hyperactive. The patient voluntarily initiates urination, but the urine stream is abruptly stopped because there is synchronization between bladder contraction and urethral relaxation, leading to incomplete voiding. Urethral obstruction can result in a similar pattern of micturition. Cerebral lesions may also result in the loss of voluntary control of micturition.

Causes of Urge Incontinence

The most common cause of urge incontinence is detrusor instability, where patients have involuntary detrusor contractions that are non-neuropathic or of unknown origin. There is no general consensus regarding the cause of detrusor instability although both a myogenic and neurologic basis have been suggested.

Detrusor instability occurs in about 75% of men with benign prostatic hyperplasia and causes frequency, urgency, and urination during the night, although incontinence itself occurs only in very severe cases. Surgical procedures, such as prostatectomy and transurethral resection of the prostate (TURP), can cause detrusor instability. Incontinence rates in TURP are very low (about 1%) but they can be significant after prostatectomy. (In the latter case, detrusor instability is usually only one of many factors involved in incontinence.)

The other common cause of overactive bladder muscle abnormalities and urge incontinence is detrusor hyperreflexia. Involuntary detrusor contractions caused by detrusor hyperreflexia may result from a central nervous system (CNS) impaired by known neurologic conditions such as stroke, multiple sclerosis, spinal cord or disk injury, dementia, or Parkinson's disease. These conditions can result in detrusor hyperactivity by interfering with the normal flow of nerve messages between the urinary system and the CNS.

Urge incontinence results from bladder contractions that overwhelm the ability of the cerebral centers to inhibit them. These uncontrollable contractions can occur because of inflammation or irritation of the bladder from calculi, malignancy, infection, atrophic vaginitis, or urethritis. Drugs that may cause or contribute to urge incontinence include diuretics and caffeine (which increase urine flow), sedative hypnotics or narcotics (which depress micturition centers in the brain), and alcohol (which also inhibits micturition centers in the brain and has a diuretic effect). Uncontrollable contractions can also occur when brain centers that inhibit contractions are inhibited by metabolic disorders such as hypoxemia and encephalopathy. Anxiety and normal aging can also cause the bladder to become overactive. Some evidence suggests that some cases are caused by ischemia (blockage of blood vessels), the same process that leads to coronary artery disease.

Disorders of the cortex may result in an overactive bladder. Functional brain scanning in healthy volunteers during micturition has demonstrated that specific areas of the frontal cortex may be involved in the micturition process. These areas have demonstrated reduced activity in elderly patients with urge incontinence.

Pathophyslology of Urge Incontinence

In a number of patients with urgency, frequency, and/or urge incontinence, the pathological process may somehow be initiated by a sustained or prolonged nociceptive signal via the somatic and/or visceral afferents (due to an underlying process such as myofascial pain or endometriosis). A prolonged nociceptive signal is believed to cause biochemical and neuropathic changes within the spinal cord, perhaps through reflexive activity within the bladder and other pelvic tissues. This process has been referred to as neurogenic inflammation, in which a neuroinflammatory process is believed to be mediated by release of vasoactive peptides such as substance P and neurokinin A.

"Neurogenic inflammation is the process whereby stimulation of peripheral nerves elicits vasodilatation, plasma extravasation, and other inflammatory changes in the skin or viscera. Neurogenic inflammation can be evoked in the bladder by antidromic stimulation of visceral afferents in the pelvic nerve. Although bladder afferents relay information to the central nervous system, they also act in the periphery to alter mucosal permeability, smooth muscle contractility, local blood flow and to influence cellular mediators of the immune system; thus an initial inflammatory event may be reinforced by neurogenic mechanisms. The resulting changes in neural processing affect the pain pathways in particular, and perturbations in the function of peripheral and central elements of the nociceptive system can be durable, outlasting the initial inflammation." [Steers W D; Tuttle J B. "Chapter 8: Neurogenic Inflammation and Nerve Growth Factor: Possible Roles in Interstitial Cystitis", in Sant G R, ed., *Interstitial Cystitis*, Lippincott Williams & Wilkins, 1997.]

With changes in spinal reflexes and the "centralization of pain," the neuropathic changes within the spinal cord become so pronounced that even with the removal of external insult, e.g., treatment of endometriosis, the neuropathic dysregulation persists. This neuropathic change explains why patients with a chronic pelvic pain syndrome may present with multiple overlapping symptoms that frequently involve pelvic pain, urgency/frequency syndrome, urge incontinence, fecal incontinence, functional bowel disease, dyspareunia, vestibulitis, and/or dysfunctional voiding.

Current Treatments

There are many surgical procedures for urinary incontinence; most are designed so pressure is exerted effectively at the neck of the bladder. The four primary procedures are retropubic suspensions (about 80% cure rate), transvaginal suspensions (60–70% cure rate), sling procedures (about 80% cure rate), and anterior repairs (60–70% cure rate). Suspensions have higher complication rates than the other procedures. Studies reported by the American Urological Association indicated that surgery should be considered as initial therapy for women with severe stress incontinence and that surgery is an effective and safe alternative when other treatments fail. Potential complications of all of these surgical procedures include obstruction of the outlet from the bladder, which causes difficulty in urination and irritation. Surgery is typically not performed in individuals with urge incontinence who have uninhibited bladder contractions.

Injections of bulking materials that help support the urethra are proving to be beneficial for people with severe stress incontinence caused by dysfunctional sphincter muscles in the urethra, but who still have good pelvic muscle support and functional bladders. The bulking agent most commonly used today is collagen, specifically animal collagen (Contigen). The collagen is injected into the tissue surrounding the urethra. The injected collagen tightens the seal of the sphincter by adding bulk to the surrounding tissue.

It is well known in the art that electrical stimulation in the region of the pelvic floor can decrease the severity of incontinence. The improvement is believed to be attained through at least three mechanisms: (1) by changing the reflex thresholds of the bladder muscles responsible for bladder emptying, (2) by strengthening the muscles that maintain closure on the bladder outlet, and (3) by changing the state of the neural pathways, musculature and/or bladder during and beyond the period of stimulus application.

The electrical stimulation therapies currently available for incontinence have generally been directed at improving muscle condition, as disclosed, e.g., in applicant's prior document WO97/18857 (PCT/US96/18680), published 29 May 1997. Bladder hyperreflexia and detrusor instability have proven more difficult to treat. However, evidence in the art suggests that it can be improved in many individuals by stimulating peripheral nerves or nerve roots continuously or intermittently to modulate transmission of excitatory nerve signals to the bladder muscles.

Several external and implantable approaches have been used to stimulate the nerves supplying the bladder and pelvic region in order to decrease the episodic incidences of unintentional bladder emptying. The approaches that strengthen periurethral muscles have usually employed vaginal or anal electrode assemblages to stimulate muscle contractions repeatedly. These methods are limited in their portability and are often poorly accepted by patients because they are inconvenient and often associated with unpleasant skin sensations. Further, the methods are inadequate for the treatment of urge incontinence in which continual electrical stimulation is commonly needed to diminish or inhibit the heightened reflexes of bladder muscles.

For the treatment of urge incontinence, surgically implanted stimulators under battery or radio-frequency control have been described in the art. These stimulators have different forms, but are usually comprised of an implantable control module to which is connected a series of leads that must be routed to nerve bundles in either the sacral roots emanating from the spinal cord, or the nerves supplying muscles, skin or other structures in the pelvic region. The implantable devices are relatively large, expensive and challenging to implant surgically. Thus, their use has generally been confined to patients with severe symptoms and the capacity to finance the surgery.

In one study, a vaginal device employing electrical stimulation was significantly more effective than a sham device for patients with urge incontinence, although there was no difference for women with stress incontinence. The Stoller Afferent Neural Stimulator (SANS) device has been applied to stimulation of the nerves above the ankle bone; more than 75% of mild to moderate incontinence patients treated in this way once a week for about a half hour reported at least 50% reduction in symptoms.

Sacral Nerve Stimulation

A sacral nerve stimulation (SNS) system (Medtronic InterStim) is available for urge incontinence, in which a battery-operated generator that produces electrical pulses is implanted in the abdomen. A wire connected to it runs to the sacral nerves in the lower back. The Sacral Nerve Stimulation Study Group compared 34 incontinence patients receiving SNS with 42 control patients who received standard medical therapy. (Reference Schmidt, et al., "Sacral nerve stimulation for treatment of refractory urinary urge incontinence. Sacral Nerve Stimulation Study Group." Journal of Urology, 1999 August; 162(2):352–7.)

At 6 months, the number of daily incontinence episodes, severity of episodes, and use of absorbent pads were significantly reduced in the stimulation group compared to the control group. Of the 34 SNS patients, 16 (47%) were completely dry and an additional 10 (29%) demonstrated a greater than 50% reduction in incontinence episodes six months after implantation. Efficacy appeared to be sustained for 18 months. During the evaluation, the group returned to baseline levels of incontinence when stimulation was inactivated. Urodynamic testing confirmed that SNS did not adversely affect voiding function. Complications included implantable pulse generator site pain in 15.9% of the patients, implant site pain in 19.1% and lead migration in 7.0%. Surgical revision was required in 32.5% of patients with implants to resolve a complication. There were no reports of permanent injury or nerve damage.

Shaker applied SNS to 16 women and 2 men with refractory urge incontinence. (See Shaker, et al., "Sacral nerve root neuromodulation: an effective treatment for refractory urge incontinence." Journal of Urology 1998 May; 159(5):1516–9.) Over an average follow-up period of 18.8 months (range 3 to 83), these patients showed a marked reduction in leakage episodes from 6.49 to 1.98 times per 24 hours. Eight patients became completely dry and 4 had average leakage episodes of 1 or less daily. Patients also demonstrated a decrease in urinary frequency with an increase in functional bladder capacity. Associated pelvic pain also decreased substantially.

The mechanism of action of sacral nerve stimulation is unknown. The afferent somatic stimulation is believed to somehow modulate the neural reflexes involved in micturition, thereby inhibiting micturition. The same inhibitory action is also believed to be responsible for the control of fecal incontinence by SNS, as described in more detail presently. SNS leads to stimulation of one or more sacral dorsal ganglia, which may also help control somatic and/or visceral pelvic pain through the same mechanism of action as spinal cord stimulation (SCS). (In SCS the non-nociceptive afferent signals are believed to "gate" or otherwise modulate central processing of nociceptive signals, via the gate control theory.) SNS may also stimulate the pelvic floor musculature and may be a form of biofeedback, enabling its use in pelvic floor rehabilitation. During typical SNS system implantation, pudendal nerve recruitment is targeted, and may be confirmed by contractions in the pelvic floor.

Malouf reported on implantation of chronic SNS systems in five women (age 41–68 years) with fecal incontinence for solid or liquid stool at least once per week. (Reference Malouf, et al., "Permanent Sacral Nerve Stimulation for Fecal Incontinence." Annals of Surgery 2000 July; 232(1): 143–148.) These patients were followed up for a median of 16 months after permanent implantation. All had incontinence, and three had urge incontinence. The cause was scleroderma in two, primary internal sphincter degeneration in one, diffuse weakness of both sphincters in one, and disruption of both sphincters in one. All patients had marked improvement. Urgency resolved in all three patients with this symptom. Passive soiling resolved completely in three and was reduced to minor episodes in two. Continence scores (scale 0–20) improved from a median of 16 before surgery to 2 after surgery. There were no early complications, and there have been no side effects. One patient required wound exploration at 6 months for local pain, and a lead replacement at 12 months for electrode displacement. The quality of life assessment improved in all patients. The resting pressure increased in four patients, but there was no consistent measured physiologic change that could account for the symptomatic improvement.

Pudendal Nerve Stimulation

Bladder contraction and micturition may be inhibited through a number of reflex arcs, some involving afferent fibers of the pudendal nerve, as discussed above. Distal branches of the pudendal nerve lead to the anal sphincter, the perineum, the urethral sphincter, the penis (in men), the vagina (in women), the glans penis (in men), and the clitoris (in women). Stimulation of the pudendal afferents from the anal sphincter has been demonstrated to inhibit bladder contraction. Similarly, stimulation of the pudendal afferents from the dorsal nerve of the penis (in men) or the dorsal nerve of the clitoris (in women) has been demonstrated to inhibit bladder contraction.

In 1974, Sundin, et al. demonstrated in cats that acute electrical stimulation of the pudendal nerve leads to detrusor inhibition. (See Sundin, et al., "Detrusor inhibition induced from mechanical stimulation of the anal region and from electrical stimulation of pudendal nerve afferents: An experimental study in cats" Investigative Urology, 1974 March; 11(5):374–8.) In 1986, Vodusek, et al. demonstrated in 8 male and 2 female patients that stimulation of the dorsal nerve of the penis or the dorsal nerve of the clitoris with surface electrodes led to bladder inhibition and an increase in bladder capacity in 8 of the 10 patients. (Reference Vodusek, et al., "Detrusor inhibition induced by stimulation of pudendal nerve afferents" Neurourology and Urodynamics, 5, 1986, 381–9.) The authors concluded that stimulation of the pudendal nerve afferents leads to detrusor inhibition in patients with neurological lesions above the sacral level.

In a 1988 study of three patients with urgency, frequency, and urge incontinence, Vodusek, et al. demonstrated that acute percutaneous electrical stimulation of the pudendal nerve at the ischial spine led to inhibition of bladder contraction and to a two- to four-fold increase in bladder capacity. The neurostimulation waveform had a frequency of 1 to 5 Hz, an amplitude of 1 to 2 mA, and a pulse width of 200 $\mu$sec. Activation of the external urethral sphincter via the efferent fibers of the pudendal nerve may also have played a role in the observed increase in bladder capacity. (See Vodusek, et al., "Detrusor inhibition on selective pudendal nerve stimulation in the perineum" Neurourology and Urodynamics. 6, 1988, 389–93.)

U.S. Pat. No. 4,607,639 (the '639 patent) discloses a method for controlling bladder evacuation via electrical stimulation of sacral roots and/or pelvic floor nerves, including the pudendal nerve. However, this method requires, first, the arduous task of, for example, "identifying the anatomical location and functional characteristics of those nerve fibers controlling the separate functions of said bladder and external sphincter." This identification is accomplished via a sacral route. Next, separating motor and sensory and/or somatic and autonomic nerve fibers is taught. Again, nerve fiber separation is accomplished via a sacral route. Additionally or alternatively to the separating of nerve fibers, the method requires isolating nerve fibers via sectioning. Again, nerve fibers are sectioned via a sacral route.

The '639 patent indicates that the method includes "identifying the anatomical location of at least one nerve." However, since one or a combination of separating, sectioning, and stimulating at least two separate nerve fibers is described, it is clear from a careful reading that the method taught in the '639 patent requires locating and identifying at least two separate neural structures. For example, one of the specific procedures of the '639 patent requires identification of both the superior somatic nerve (which innervates the levator ani muscles) and the inferior somatic nerve (innervating the pudendal nerve at Alcock's canal), so that the superior somatic nerve may be sectioned and the inferior somatic nerve may be stimulated. As another example, the S3 sacral nerve is identified, then the ventral and dorsal roots are surgically separated (which requires their identification), so the ventral root alone may be stimulated. Other specific procedures require the stimulation of at least two separate neural structures, such as the inferior somatic nerve and the S3 ventral root (separated from the dorsal root). Such procedures may reasonably be expected to be more time-consuming than the identification and stimulation of a single neural structure. The '639 patent does not teach a method in which identification of only one neural structure is necessary, e.g., identification of a single nerve such as the pudendal nerve, which directly controls the function of the external sphincter and not the bladder.

Further, all the surgical procedures described in the '639 patent are performed via a sacral approach. A plethora of pelvic area nerves emanate from the sacral segments. Therefore, stimulation of the neural structures targeted by the '639 patent via a sacral route results in 1) needing to identify which nerves to stimulate, separate, or section, and 2) the actual separating and sectioning of physically and/or physiologically close nerve fibers. Thus, it is not surprising that the surgical procedures of the '639 patent are complicated by the identifying, separating, and sectioning of multiple nerves. In addition, it is difficult or impossible to reach portions of some nerves via a sacral approach, such as the portion of the pudendal nerve that passes through Alcock's canal.

Additionally, the '639 patent describes only radio-frequency control of an implanted stimulating electrode.

Many of the therapies described above have been used to treat pelvic pain, with the same drawbacks. For instance, neurostimulation of the sacral nerve roots has been demonstrated to relieve pelvic pain in patients with intractable chronic pelvic pain. Other devices used for both incontinence and pelvic pain require that a needle electrode(s) be inserted through the skin during stimulation sessions. These devices may only be used acutely, and may cause significant discomfort.

What is needed are ways to effectively use implantable stimulators to chronically stimulate the pudendal nerve and its branches directly, for treating incontinence and/or pelvic pain.

SUMMARY OF THE INVENTION

The systems and methods taught in this invention include the injection, direct implantation, endoscopic, or laparoscopic implantation of one or more battery- or radio-frequency-powered microstimulators beneath the skin of the perineum. The systems and methods taught also include the injection, direct implantation, endoscopic, or laparoscopic implantation of one or more battery- or radio-frequency-powered microstimulators on or near the tibial nerve. The systems and methods taught also include implantation of other, various means for chronically stimulating the pudendal nerve and/or its branches.

The devices are programmed using, e.g., radio-frequency control via an external controller that can be used by a physician to produce patterns of output stimulation pulses judged to be efficacious by appropriate clinical testing. Such stimulation program is retained in the device or external controller and is transmitted when commanded to start and stop by a signal from the patient or caregiver.

It is an object of this invention to reduce or eliminate the incidence of unintentional episodes of bladder emptying (i.e. incontinence) as well as other dysfunctions of perineal structures, such as urgency and frequency, by stimulating nerve pathways that diminish involuntary bladder contractions, improve closure of the bladder outlet, and/or improve the long-term health of the urinary system by increasing bladder capacity and thus, the time period between emptying. As one example of another dysfunction of perineal structures, it is also an object of this invention to similarly reduce or eliminate the incidence of fecal incontinence.

Another object of this invention is to reduce or eliminate pelvic pain by chronically stimulating nerve pathways, such as those that derive from the sacral roots, using an implantable neurostimulator that is implanted with a minimal surgical procedure.

It is a further object of this invention to teach a method whereby a patient can receive one or more patterns of neural stimulation that can be prescribed by a physician and administered without continuous oversight by a clinical practitioner.

It is a feature of some embodiments of the invention to meet one or more of the above-identified objects of the invention using stimulation systems and methods for chronically stimulating the pudendal nerve and/or its branches directly, rather than indirectly by sacral nerve stimulation.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1:
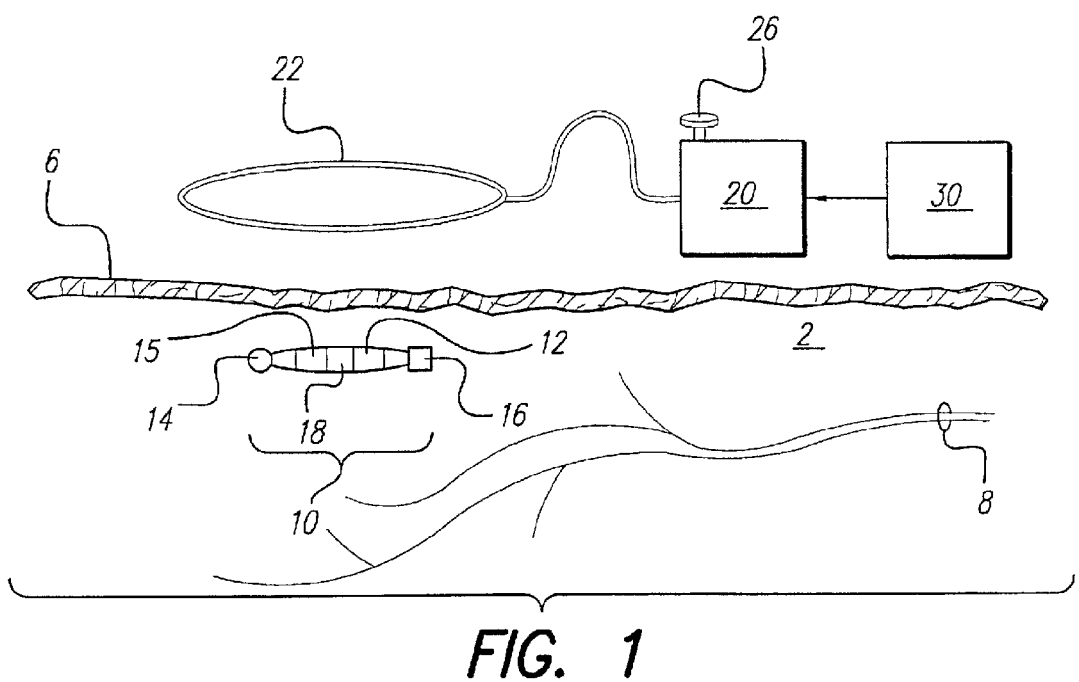
FIG. 1 illustrates a programming system for use with an implantable microstimulator.

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention reduces or eliminates incontinence and/or pelvic pain by stimulating various nerve pathways with various stimulation systems and methods. For example, the present invention includes a system for using one or more stimulating drugs and/or electrical stimulation to directly activate the pudendal nerve and/or its branches by means of an implantable signal generator and electrode(s) and/or an implantable pump and catheter(s). One or more electrodes may be surgically attached to the nerve(s) or implanted adjacent to the nerve(s) to provide electrical stimulation, and/or one or more catheters may be surgically attached to the nerve(s) or implanted adjacent to the nerve(s) to infuse a stimulating drug(s). The stimulating electrode(s) and/or the infusing catheter(s) may be attached to or placed adjacent to any part of the pudendal nerve, including a portion in the pudendal canal and/or any of the distal branches, such as the dorsal nerve of the penis or clitoris. (As used herein, "near" and "adjacent" mean as close as reasonably possible to targeted tissue, including touching or even being positioned within the tissue, but in general, may be as far as can be reached with the stimulation pulses.)

Also, herein, stimulating drugs comprise medications, anesthetic agents, synthetic or natural hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

When a sensory nerve is stimulated, it produces an electrical impulse that is transmitted along the axon into the dorsal horn of the spinal cord, where it can produce perceptible sensations, modulation of spinal cord circuits, and reflex effects on motor pathways. When a motor nerve is stimulated, electrical impulses are conveyed through its many peripheral branches that supply muscle fibers and elicit contractions in them.

A preferred stimulation location for purposes of the present invention is the pelvic floor. Direct stimulation of the pelvic floor nerves bypasses the potential recruitment of other unrelated nerve groups at the sacral roots. Nerves in this region that may be targeted for stimulation include the pudendal nerve, pelvic nerve, and branches of the pudendal nerve.

The pudendal nerve and its branches are somatic nerves that originate from the sacral nerve roots S2, S3, and S4. These and other somatic nerves emanating from the sacral nerve roots are preferably stimulated to treat dysfunctions of perineal structures, such as urinary and/or bowel incontinence, urgency, frequency, and/or pain. For instance, stimulation of the urethral branch of the pudendal nerve may be used to inhibit defecation, thereby treating fecal incontinence. Additionally or alternatively, stimulation of the inferior rectal branch of the pudendal nerve, which innervates the external anal sphincter, may also inhibit defecation, thereby treating fecal incontinence. Stimulation of other somatic nerves innervating the rectum and/or colon may treat constipation, fecal retention, and/or colorectal hypomotility. Stimulation of one or more other pudendal nerve branches (e.g., the dorsal nerve of the clitoris/penis) may be used as a treatment of, e.g., urinary urge incontinence and/or detrusor hyperreflexia. Stimulation of nerves innervating the urethra and/or detrusor muscle may treat urinary retention, while stimulation of nerves innervating the internal and/or external urethral sphincter or their intramuscular branches may treat urinary stress incontinence. Stimulation of nerve(s) innervating the clitoris and/or vagina may treat vaginismus, dyspareunia, anorgasmia, or other female sexual dysfunction.

In some embodiments of the present invention, pudendal nerve stimulation is performed at the pudendal canal, a.k.a. Alcock's canal, where the nerve hooks around the ischial spine. As will be evident to those of skill in the art, other locations along the pudendal nerve, and along its branches, may also/alternatively be stimulated. The location of the pudendal canal may be readily discerned by a physician, as the ischial spine may be palpated transvaginally in most patients. A stimulation device may thus be guided to this area using the ischial spine as a landmark. As described in more detail presently, such a device may be introduced transvaginally or transperineally, or via other approaches, such as transrectally, that will be readily apparent to those skilled in the art upon reading the present disclosure. The ischial spine may also be visualized via diagnostic imaging, e.g., CT scan, and such imaging may be used to guide an electrode(s) to the ischial spine and thus a targeted location, e.g., the pudendal canal.

As mentioned above, distal branches of the pudendal nerve lead, e.g., to the anal sphincter, the perineum, the urethral sphincter, the penis (in men), the vagina (in women), the glans penis (in men), and the clitoris (in women). Branches of the pudendal nerve may be easily accessed percutaneously, and as described earlier, selective stimulation of a given branch(es) may offer advantages for the treatment of certain disorders. An advantage of directly stimulating the pudendal nerve and/or its branches is the resulting recruitment of sacral nerves S2, S3, and S4. In addition, the stimulation of the present invention leads to less side effects than, e.g., sacral nerve stimulation. For instance, stimulating the pudendal nerve and/or its branches avoids recruitment of nerves unrelated to the desired treatment, such as the sciatic nerve.

Another preferred stimulation location for purposes of the present invention is the tibial nerve. The tibial nerve is relatively easily accessible (i.e., relatively near the overlying skin with no muscle between the nerve and the skin) at two sites in the leg: at the level of the ankle, immediately posterior to the medial malleolus and posterior tibial artery and vein; and at the level of the knee, in the popliteal fossa (i.e., the back of the knee), immediately lateral to the popliteal artery and vein. Other sites along the tibial nerve, although not as easily accessible, are acceptable stimulation sites. Unilateral or bilateral stimulation is possible. For instance, a microstimulator may be implanted unilaterally, or two or more microstimulators may be implanted bilaterally.

If electrical stimulation is applied by a stimulator, the electrodes may be configured on one or more leads attached to an implantable pulse generator (IPG), as described in more detail presently, or the stimulator may be configured as a microstimulator, such as described below. Similarly, a drug infusion system may be included as part of the electrical stimulator or in a separate stimulator with a reservoir and one or more catheters for infusion, or alternatively a stimulator may comprise a microstimulator with a self-contained microinfusion pump that delivers the drug(s).

Some embodiments of the present invention utilize one or more implantable microstimulators. Some microstimulators used with the present invention are preferably of the type referred to as BION® devices, while other small stimulators may alternatively be used with the present invention. The following documents describe various features and details associated with the manufacture, operation and use of BION microstimulators, and are all incorporated herein by reference:

| Application/Patent/ Publication No. | Filing/Publication Date | Title |
|---|---|---|
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued Jun. 28, 1994 | Implantable Microstimulator |
| U.S. Pat. No. 5,405,367 | Issued Apr. 11, 1995 | Structure and Method of Manufacture of an Implantable Microstimulator |
| PCT Publication WO 98/37926 | published Sep. 3, 1998 | Battery-Powered Patient Implantable Device |
| PCT Publication WO 98/43700 | published Oct. 8, 1998 | System of Implantable Devices For Monitoring and/or Affecting Body Parameters |
| PCT Publication WO 98/43701 | published Oct. 8, 1998 | System of Implantable Devices For Monitoring and/or Affecting Body Parameters |
| U.S. Pat. No. 6,051,017 (application Ser. No. 09/077,662) | Issued Apr. 18, 2000 | Improved Implantable Microstimulator and Systems Employing Same |
| | published September 1997 | Micromodular Implants to Provide Electrical Stimulation of Paralyzed Muscles and Limbs, by Cameron, et al., IEEE Transactions on Biomedical Engineering, Vol. 44, No. 9, pages 781–790. |

A microstimulator, when used, is preferably implanted with a surgical insertion tool specially designed for the purpose, or is injected (e.g., via a 12 gauge hypodermic needle, or similar device), in or around nerves and muscles. Alternatively, the device may be implanted via conventional, endoscopic, or laparoscopic surgical techniques. Advantageously, the small size of the microstimulators referenced above permits insertion of these devices beneath the skin of the perineum, for instance, where they have the capability to stimulate the nerves and muscles in regions surrounding the urethra and anus. A more complicated surgical procedure may be required for fixing the neurostimulator in place.

The microstimulators of the type described in the referenced patents and patent publications represent a new class of generic implantable stimulators. While each microstimulator is a single programmable unit, the same external unit may control up to 256 stimulators that then work in harmonious combination to create a neuromuscular control network. Because the microstimulators are injectable, they are minimally invasive, and are preferably injected in an outpatient environment posing little clinical risk, and reducing costs. If necessary, such microstimulators may be removed through a small surgical incision.

In one preferred embodiment, the microstimulator configured for electrical stimulation comprises two, leadless electrodes. However, either or both electrodes may alternatively be located at the ends of short, flexible leads as described in U.S. patent application Ser. No. 09/624,130, filed Jul. 24, 2000, which is incorporated herein by reference in its entirety. The use of such leads may permit electrical stimulation to be directed more locally to targeted tissue(s) a short distance from the surgical fixation of the bulk of the implantable stimulator, while allowing most elements of the microstimulator to be located in a more surgically convenient site. This minimizes the distance traversed and the surgical planes crossed by the device and any lead(s). In a preferred embodiment, the leads are no longer than about 100 to 120 mm.

For some patients, use of a stimulator for only a few hours per day or week will improve the symptomatology of incontinence and/or pelvic pain. In such patients, radiofrequency (RF) controlled devices provide an adequate amount of stimulation if used intermittently, e.g., for only a few hours per day, to greatly decrease the incidence of incontinent and/or painful episodes. For many other patients, however, a continuous or intermittent stimulation throughout the day is needed. These patients may best utilize a stimulator that has a self-contained power source sufficient to deliver repeated pulses for several hours and that can be recharged repeatedly, if necessary. In accordance with the teachings of the present invention, the use of a stimulator with a rechargeable battery thus provides these patients the portability needed to free the patient from reliance on RF power delivery.

A battery-powered microstimulator suitable for use with the present invention, and a control system for use with such battery-powered microstimulator, is fully described in earlier referenced WO 98/37926, published 3 Sep. 1998; WO 98/43700, published 8 Oct. 1998; and WO 98/43701, published 8 Oct. 1998. Other microstimulators are suitable for use with the present invention, such as a microstimulator with a self-contained microinfusion pump for delivering drug(s). Additional electrical and drug infusion stimulator systems and methods suitable for use with the present invention are described herein.

For purposes of this patent application, it is sufficient to note that RF controlled stimulators receive power and control signals from an extra corporeal antenna coil via inductive coupling of a modulated RF field. Battery-operated stimulators incorporate a power source within the device itself but rely on RF control, inductive linking, or the like to program stimulus sequences and to recharge the power source, when needed. In accordance with the present invention, each implanted stimulator may be commanded to produce an electrical and/or infusion pulse of a prescribed magnitude and duration and at a repetition rate sufficient to cause stimulation of nerve axons.

Turning to FIG. 1, a preferred embodiment of the invention is illustrated. A rechargeable, battery-powered microstimulator 10 is implanted under the skin 6, into subcutaneous region 2, where current pulses delivered from its electrodes 14 and 16 stimulate nerve fibers 8. Nerve bundles in the subcutaneous region may carry somatic sensory axons supplying receptors in skin and muscle and somatic motor axons supplying skeletal muscle, as well as autonomic axons supplying visceral and glandular structures and smooth muscle.

Microstimulator 10, and all stimulators configured in accordance with the present invention (e.g., see FIG. 5), preferably contains electronic circuitry 12 for receiving data and/or power from outside the body by inductive, RF, or other electromagnetic coupling. In a preferred embodiment, electronic circuitry 12 includes an inductive coil for receiving and transmitting RF data and/or power, an integrated circuit (IC) chip for decoding and storing stimulation parameters and generating stimulation pulses (either intermittent or continuous), and additional discrete electronic components that may be required to complete the electronic circuit functions, e.g., capacitor(s), resistor(s), coil(s), and the like.

Electronic circuitry 12 dictates the amplitude and duration of the electrical current pulse, when used, thereby determining the number of nerve fibers excited by each pulse. Advantageously, electronic circuitry 12 includes a programmable memory 18 for storing a set(s) of data, stimulation, and control parameters. This feature allows electrical and/or drug stimulation to be adjusted to settings that are safe and efficacious with minimal discomfort for each individual. Specific parameters may provide therapeutic advantages for various levels and types of incontinence and/or pain. For instance, some patients may respond favorably to intermittent stimulation, while others may require continuous treatment for relief. Electrical and drug stimulation parameters are preferably controlled independently. However, in some instances, they are advantageously coupled, e.g., electrical stimulation may be programmed to occur only during drug infusion.

Preferred implantable stimulators also include a power source and/or power storage device 15. Possible power options for a stimulation device(s) of the present invention, described in more detail below, include but are not limited to an external power source coupled to the stimulation device, e.g., via an RF link, a self-contained power source utilizing any means of generation or storage of energy (e.g., a primary battery, a replenishable or rechargeable battery such as a lithium ion battery, an electrolytic capacitor, or a super- or ultra-capacitor), and if the self-contained power source is replenishable or rechargeable, means of replenishable or recharging the power source (e.g., an RF link).

In a preferred embodiment illustrated in FIG. 1, electronic circuitry 12 receives operating power, recharge power for the battery (if a rechargeable battery is included within the stimulator), and data to be stored in memory element 18 by inductive coupling from external controller 20 and its associated antenna coil 22. During an initial programming session after implantation of stimulator 10, the prescribing physician uses a programming station 30 to download a pattern of stimulus pulse delivery to controller 20, which saves the information in nonvolatile memory. Each time stimulator(s) 10 are recharged by controller 20, the stimulation parameters required from each stimulator 10 are transmitted via coil 22, along with the power required for recharging. The stimulation parameters are stored in memory element 18 of each stimulator 10 as long as power storage device 15 has sufficient power to operate the stimulator circuitry.

According to the preferred embodiment of FIG. 1, program delivery is initiated by start and stop commands delivered by patient-governed control switch 26. In this and other preferred embodiments, controller 20 is a module, preferably handheld, containing a microprocessor and appropriate nonvolatile memory, such as electronically erasable programmable read-only-memory (EEPROM). In additional preferred embodiments, controller 20 operates to control implantable stimulator 10 by any of various means, including sensing the proximity of a permanent magnet located in controller 20, or sensing RF transmissions from controller 20. However, it will be evident to those of skill in electronic circuitry and computing that many different system architectures and components could be used to achieve similar functionality with either a battery-powered or RF-powered microstimulator device.

Figure 2:
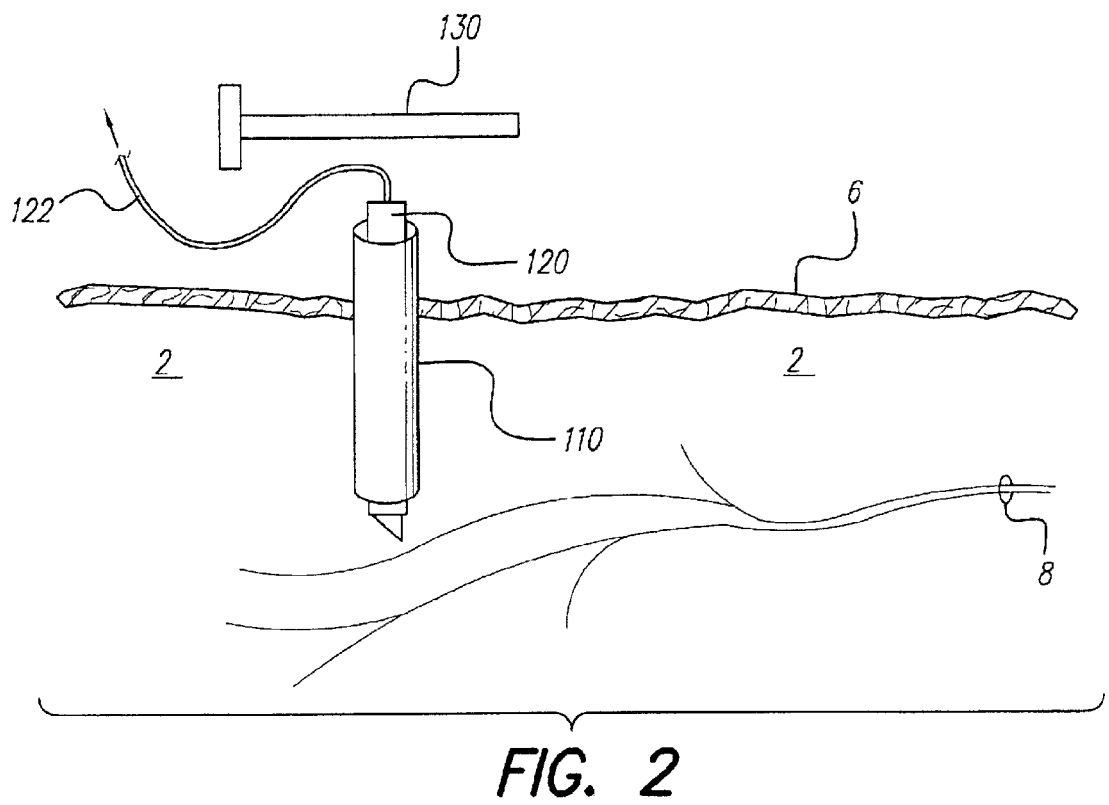
FIG. 2 shows an insertion system for use with an implantable microstimulator and an exemplary location for the microstimulator.

In accordance with one embodiment of the present invention, a microstimulator is injected into soft tissues by using an insertion device such as is shown in FIG. 2. The hollow cannula 110 of the insertion device is comprised of a stiff, dielectric material with sufficient lubricity to permit the undamaged passage of device 10 therethrough. Probe 120 is a rigid, electrically conductive trocar whose sharply pointed end extends beyond the end of the tube. The trocar is used to deliver electrical impulses to the tissue at its end. Electrical stimuli can be delivered by means of the trocar 120 by connecting an electrical stimulator (not shown) to connector 122 on the trocar. The initial insertion site of the trocar, guided by a clinical knowledge of tissue landmarks or radiographic images, may be modified until stimulation produces excitation of nerves 8 judged by perceptible sensations or clinical demonstration of desired effects on bladder, periurethral muscle or other pelvic floor musculature. Satisfactory stimulation of nerves 8 will ensure that the end of the rod around the trocar is located in an appropriate site sufficiently close to nerves 8 so that electrical stimulation using the microstimulator will also produce the desired nerve excitation. Insertion of the microstimulator is accomplished by removing trocar 120 and passing the microstimulator through the hollow cannula 110 using, e.g., a blunt-ended push-rod 130.

Figure 3:
FIG. 3 depicts additional exemplary locations for the implantable stimulator.

As mentioned earlier and as depicted in FIG. 3, another preferred stimulation location for purposes of the present invention is on or adjacent the tibial nerve 140. The tibial nerve is relatively easily accessible (i.e., relatively near the overlying skin with no muscle between the nerve and the skin) at two sites in the leg. The first is at the level of the ankle, immediately posterior to the medial malleolus 144, the posterior tibial artery 146, and the posterior tibial vein 148. The second is at the level of the knee, in the popliteal fossa (i.e., the back of the knee), immediately lateral to the popliteal artery 152 and the popliteal vein 154. Other sites along tibial nerve 140, although not as easily accessible, are acceptable stimulator locations.

Figure 4:
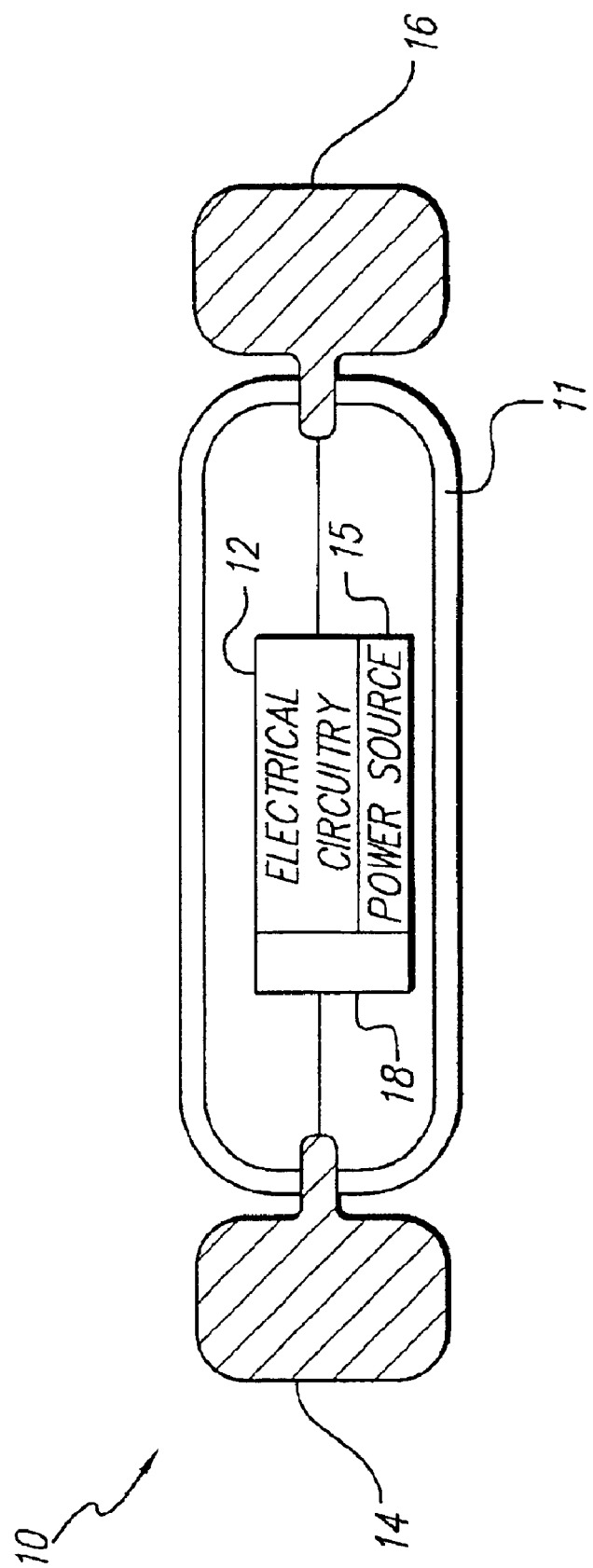
FIG. 4 illustrates an exemplary embodiment of a stimulation system of the present invention.

As depicted in FIG. 4, a preferred microstimulator 10 includes a narrow, elongated capsule 11 containing electronic circuitry 12 connected to electrodes 14 and 16, which pass through the walls of the capsule at either end. As detailed in the referenced patents, electrodes 14 and 16 comprise a stimulating electrode (to be placed close to the nerve) and an indifferent electrode (for completing the circuit). Other configurations of microstimulator 10 are possible, as is evident from the above-referenced patents.

The preferred microstimulator 10 should be sufficiently small to permit its placement near the structures to be stimulated. Capsule 11 preferably has a diameter no greater than about 3–4 mm, and more preferably only about 1.5 mm. Capsule length is preferably no greater than about 20–25 mm, and more preferably only about 10–12 mm. The shape of the microstimulator is preferably determined by the structure of the desired target, the surrounding area, and the method of surgical insertion. A thin, elongated cylinder with electrodes at the ends, as shown in FIG. 4, is currently preferred, but other shapes, such as spheres, disks or helical structures, are possible.

The external surfaces of, e.g., stimulator 10 are advantageously composed of biocompatible materials. For instance, capsule 11 is preferably made of, e.g., glass, ceramic, or other material that provides a hermetic package that will exclude water vapor but permit passage of electromagnetic fields used to transmit data and/or power. Stimulating electrodes are preferably made of a noble or refractory metal or compound, such as platinum, iridium, tantalum, titanium, titanium nitride, niobium, or alloys of any of these, in order to avoid corrosion or electrolysis which could damage the surrounding tissues and/or the device.

As mentioned earlier, stimulation is provided in accordance with the teachings of the present invention by electrical stimulation and/or a stimulating drug(s). The invention includes one or more stimulators. In the case of electrical stimulation only, preferred stimulators include a microstimulator(s) and/or an implantable pulse/signal generator (IPG). In the case of drug infusion only, preferred stimulators include an implantable pump or a microstimulator comprising a microinfusion pump. In cases requiring both electrical stimulation and drug infusion, one or more stimulators are used. Alternatively and preferably, when needed, a stimulator provides both electrical stimulation and one or more stimulating drugs.

Figure 5:
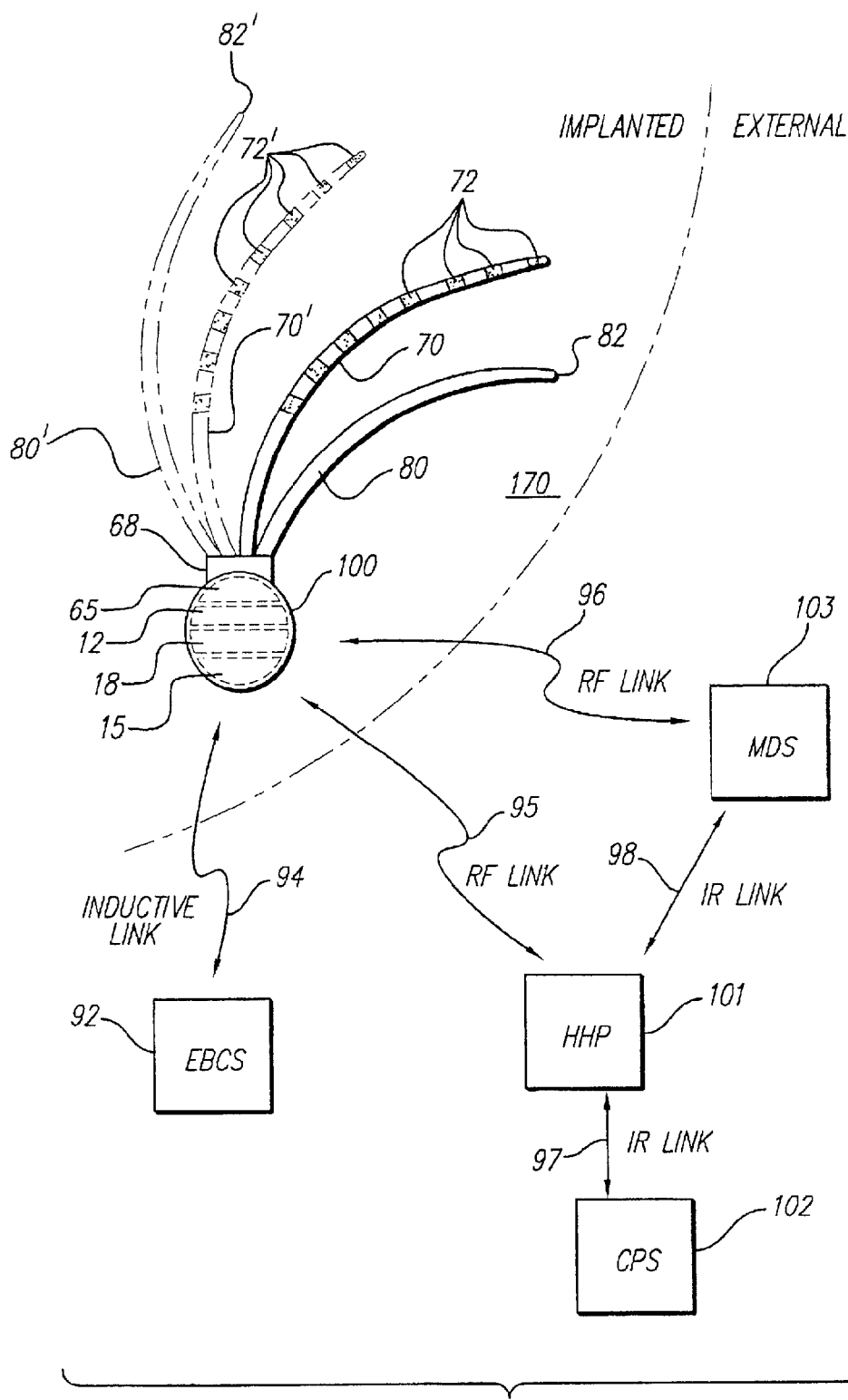
FIG. 5 illustrates an additional exemplary embodiment of a stimulation system of the present invention and an exemplary embodiment of external components of the invention.

Stimulator 100, depicted in FIG. 5, is preferably implanted in a surgically-created shallow pocket remote from the stimulation site, such as in the thigh or flank, more preferably in the buttocks, and most preferably in the abdomen. Stimulator 100 preferably conforms to the profile of surrounding tissue(s) and/or bone(s), and is small and compact. This is preferable so that no unnecessary pressure is applied to the surrounding tissues or skin, as this may result in skin erosion or infection. Stimulator 100 preferably has a diameter of no greater than 75 mm, more preferably no greater than 65 mm, and most preferably about 35–55 mm. Stimulator thickness of approximately 10–12 mm is preferred, while a thickness of about 8–10 mm or less is more preferred.

One or more electrode leads 70 and/or catheters 80 attached to stimulator 100 run subcutaneously, preferably in a surgically-created tunnel(s), to the tissues to be stimulated. As previously mentioned, sacral nerve stimulation has commonly been used to recruit the pudendal nerve and/or its branches, while the present invention teaches systems and methods for direct, chronic stimulation of these nerves with a fully implanted stimulator.

Figure 6A:
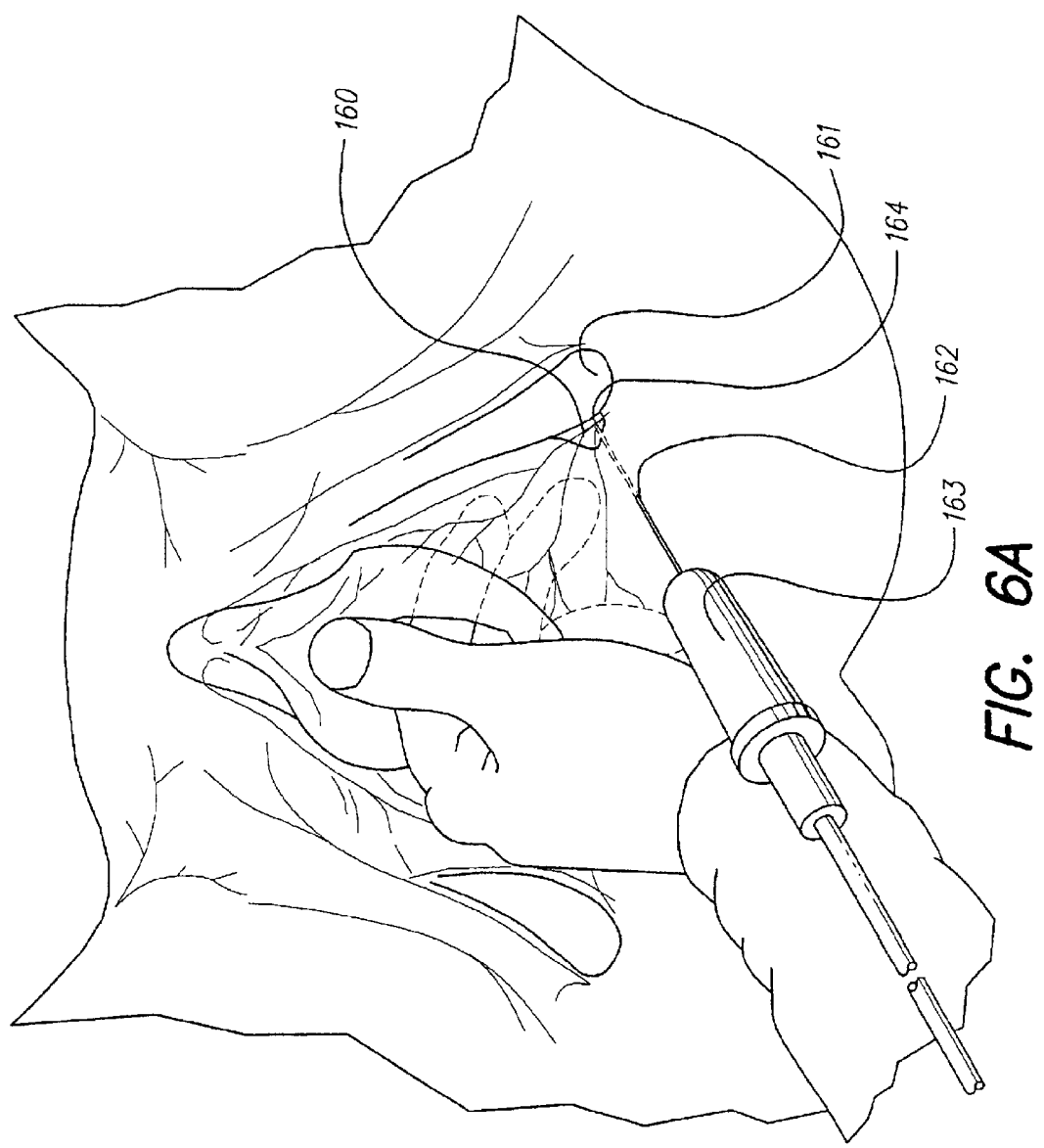
FIG. 6A depicts a preferred approach, according to the instant invention, for advancing an insertion tool toward the pudendal nerve.
Figure 6B:
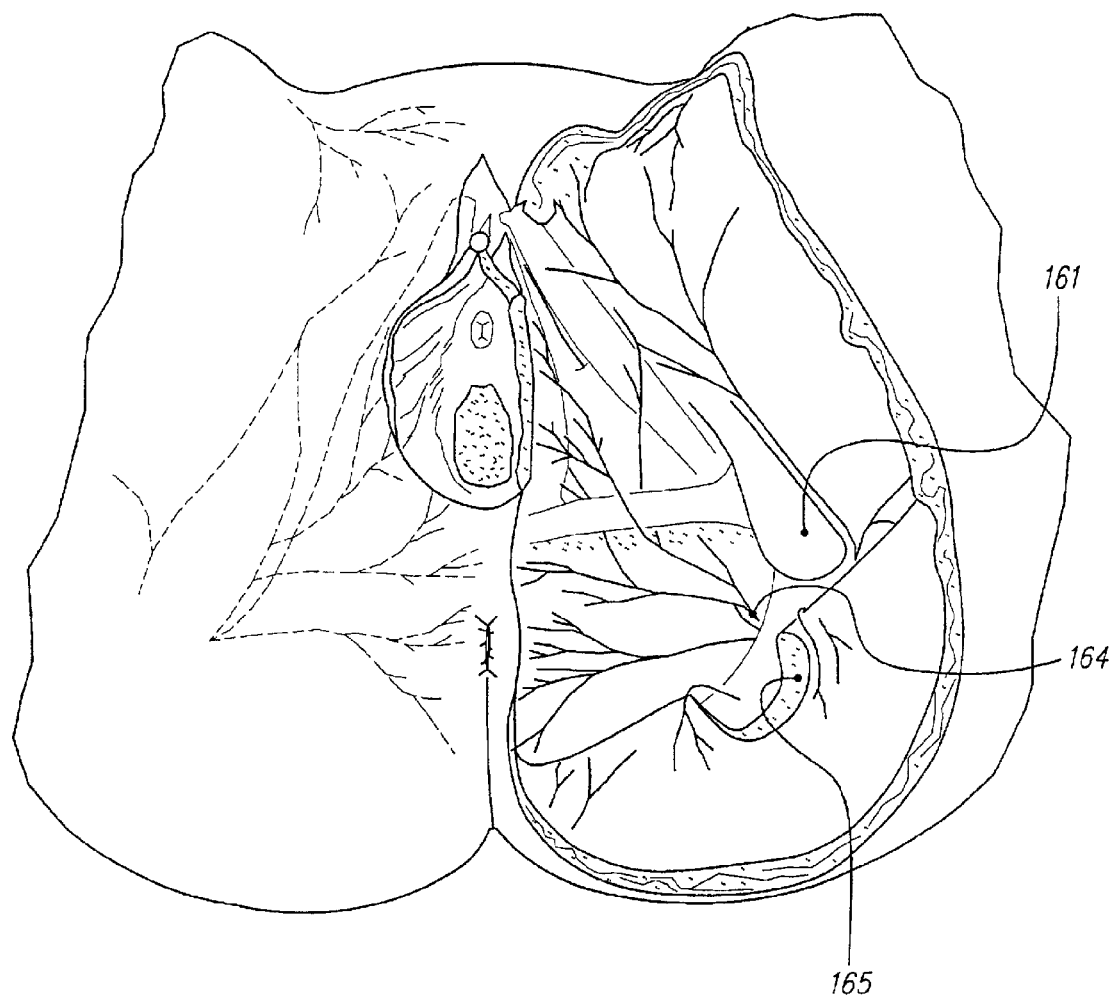
FIG. 6B is a partial dissection depicting various bones, nerves, muscles, and other tissues of the female perineum.

One approach for implantation of a lead(s) and/or catheter(s) at the pudendal nerve and/or its branches is herein referred to as the perineal approach. In the following steps, placement of the electrodes on a lead or of the discharge (end) portion of a catheter is stated simply as placement of a lead or catheter. As mentioned earlier, described in more detail below, and as seen in FIG. 6A, the ischial spine 160 may be used as a landmark for locating the pudendal nerve, as may the ischial tuberosity 161 (visible in FIGS. 6A, 6B, and 6C). The perineal approach for a female patient preferably involves the following steps.

Figure 6C:
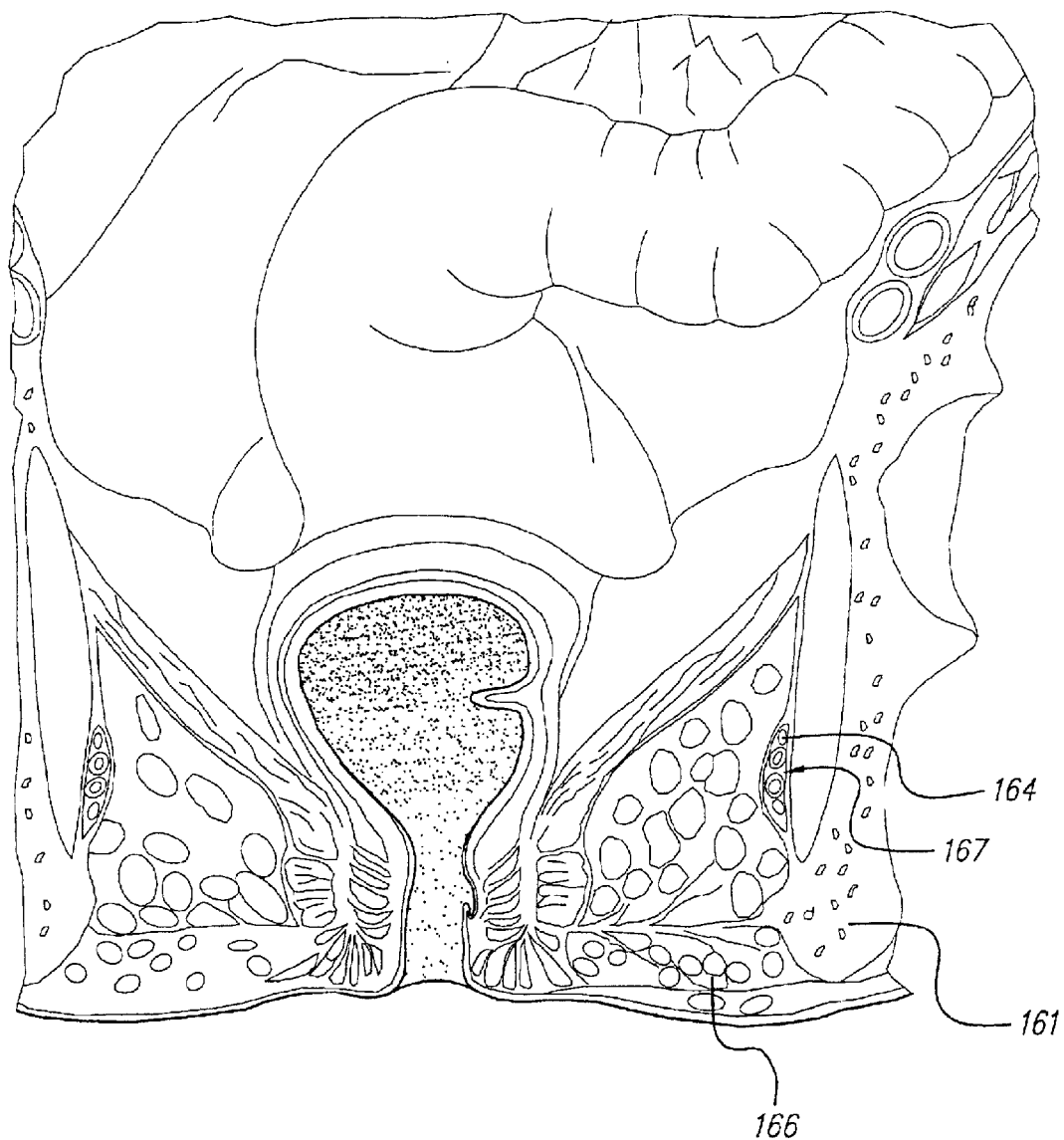
FIG. 6C is a dissection depicting various bones, nerves, muscles, vessels, and other tissues of the ischioanal fossa.

1. Locate the ischial tuberosity (IT) 161 through the skin. As best seen in FIG. 6C, a portion of IT 161 lies close to the surface of the skin.
2. Mark the skin 1–5 mm medial from IT 161. This defines the site 162 for inserting a tool 163 for lead/catheter placement.
3. As depicted in FIG. 6A, locate the ischial spine (IS) 160 by inserting one or two fingers into the vagina (or anus) and palpating laterally (a procedure known in the medical arts). The pudendal nerve 164 in the pudendal canal 167 (FIG. 6C) lies adjacent to IS 160.
4. Guide the insertion tool 163 toward IS 160. Use finger pressure against the vaginal (or anal) wall to track insertion of tool 163 from the marked insertion site 162 toward IS 160.
5. Using techniques known in the art, optionally perform test stimulation to confirm proper lead and/or catheter location, to confirm response, and/or to determine preliminary stimulator settings. (This test stimulation may be referred to as an acute trial, an operating room trial, or a procedure room trial, and may last from minutes to hours.) For instance, the insertion tool may include a tip electrode, or electrodes of a lead inserted through the tool, or drugs delivered through a catheter may be used to deliver stimulation while analyzing patient response. Alternatively, a Chalgren 23 gauge, 137 mm long Teflon™ monopolar needle electrode (available from Jari Electrode Supply of Gilroy, Calif.), or the like, may be used. Response(s) may include patient report of sensation, vaginal EMG, urethral sphincter PeNTML and/or anal sphincter PNTML, or other methods known in the art.
6. Once at the desired location, deposit the lead and/or catheter. Depending on the type of tool and lead/catheter used, this may include pushing the lead/catheter out a cannula, and/or expelling a biocompatible adhesive to help secure the lead/catheter to surrounding tissue, and/or expelling a lead/catheter with self-securing barbs, and/or securing the lead/catheter with an anchor, sutures, or the like to subcutaneous muscle 165 (FIG. 6B), fascia 166 (FIG. 6C), or other tissue within an incision at the insertion site or anywhere along the lead/catheter path, or via other methods known in the art.
7. Once the lead/catheter is deposited and/or anchored, again optionally perform test stimulation to confirm the lead/catheter has not shifted out of position. Repeat any steps required to reposition the lead/catheter.
8. If not removed while securing the lead/catheter, remove tool 163.

One additional approach for implantation of a lead(s) and/or catheter(s) at the pudendal nerve and/or its branches, as mentioned earlier, is herein referred to as the vaginal approach, which preferably involves the following steps.

1. Optionally, grossly locate pudendal nerve 164 in the pudendal canal by inserting one or two fingers into the vagina and palpating laterally to locate IS 160.
2. Insert a speculum into the vagina.
3. With the speculum inserted, again, optionally, grossly locate pudendal nerve 164 in the pudendal canal by inserting one or two fingers into the vagina and palpating laterally to locate IS 160.
4. Guide the insertion tool 163 through the vaginal wall and toward IS 160.
5. Using techniques known in the art, optionally perform test stimulation to confirm proper lead and/or catheter location, to confirm response, and/or to determine preliminary stimulator settings, as described above.
6. Once at the desired location, deposit the lead and/or catheter, as described above. The lead/catheter may be fixed in place as described earlier, or by anchoring to tissue exposed through an incision made in the vaginal wall.
7. Once the lead/catheter is deposited and/or anchored, again optionally perform test stimulation to confirm the lead/catheter has not shifted out of position. Repeat any steps required to reposition the lead/catheter.
8. If not removed while securing the lead/catheter, remove the speculum and tool 163.

Once the electrodes of the lead(s) and/or catheter end portion(s) are in place, a lead/catheter tunnel(s) will be made, either to a stimulator implantation site, or possibly to a percutaneous trial exit site if a percutaneous trial is conducted prior to implanting a chronic stimulator. A trial period will more likely be used with patients being treated for pain, but may also be used with patients being treated for incontinence. To tunnel to a percutaneous trial exit site, the following steps are preferred:

1. Locate and mark the percutaneous trial exit site. Various locations are adequate, but a site that is contralateral and symmetrical to the planned stimulator implant site is preferred.
2. Either run a tunneling tool from the lead/catheter implantation site to the marked percutaneous trial exit site or run a tunneling tool from the marked percutaneous trial exit site to the lead/catheter implantation site. In either case, the tunnel should be subcutaneous (i.e., just under the skin), or in some cases, may be deeper. If necessary, an incision(s) may be made to tunnel in sections, as may be needed if a lead/catheter extension(s) is used. Tunneling to/from the pudendal nerve and its branches is new, however, the tunneling tools and methods known in the art may be adapted for this use.
3. Using techniques known in the art, pull lead(s)/catheter(s)/extension(s) through the tunnel or tunnel sections. As appropriate, connect any extension(s) to the implanted catheter/lead. The lead(s)/catheter(s)/extension(s) may be pulled either from the lead/catheter implantation site or from the percutaneous trial exit site. For trial stimulation, it is preferable, but not required, that a percutaneous extension be pulled from the exit site to the lead/catheter implantation site, where the extension is connected to the implanted catheter/lead. (When trial stimulation is complete, the connector may be cut off the percutaneous extension so the extension can be pulled back through the percutaneous exit site to reduce infection risk.) The proximal end of the lead(s)/catheter(s)/extension(s) (which attaches to the trial stimulator) should extend from the marked percutaneous trial exit site.
4. Attach the proximal end of the lead(s)/catheter(s)/extension(s) to the trial stimulator.
5. Optionally perform test stimulation to confirm proper lead and/or catheter location, proper trial stimulator function, and/or to determine preliminary stimulator settings. Again, response(s) may include patient report of sensation, vaginal EMG, urethral sphincter PeNTML and/or anal sphincter PNTML, or other methods known in the art.
6. Surgically close the skin at the lead/catheter implantation site and around the lead/catheter/extension at the percutaneous trial exit site, using techniques known in the art.

To tunnel to a stimulator site and implant the stimulator, the following steps are preferred:

1. Locate and mark the stimulator implantation site.
2. Either run a tunneling tool(s) from the lead/catheter implantation site to the marked stimulator implantation site or make an incision at the stimulator implantation site and run a tunneling tool(s) from the incision to the lead/catheter implantation site. In either case, the tunnel(s) should be subcutaneous, or in some cases, may be deeper. If necessary, an additional incision(s) may be made to tunnel in sections, as may be needed if a lead/catheter extension(s) is used. Again, tunneling to/from the pudendal nerve and its branches is new, however, the tunneling tools and methods known in the art may be adapted for this use.
3. Using techniques known in the art, pull lead(s)/catheter(s)/extension(s) through the tunnel or tunnel sections. As appropriate, connect any extension(s) to the implanted catheter/lead. The lead(s)/catheter(s)/extension(s) may be pulled either toward the lead/catheter implantation site or toward the stimulator implantation site until the proximal end of the lead(s)/catheter(s)/extension(s) (which attaches to the stimulator) extends from the marked stimulator implantation site.
4. Attach the proximal end of the lead(s)/catheter(s)/extension(s) to the stimulator.
5. Optionally perform test stimulation to confirm proper lead and/or catheter location, proper stimulator function, and/or to determine preliminary stimulator settings. Again, response(s) may include patient report of sensation, vaginal EMG, urethral sphincter PeNTML and/or anal sphincter PNTML, or other methods known in the art.
6. Implant the stimulator using standard techniques known in the art.
7. Surgically close the skin at the stimulator implantation site and at the lead/catheter implantation site, using techniques known in the art.

Referring again to FIG. 5, in the case of treatment with electrical stimulation, electrode(s) 72 are carried on lead 70 having a proximal end coupled to stimulator 100. Electrode(s) 72 may include a tip electrode and may include one or more ring electrodes, allowing bipolar stimulation and/or compensation for any migration of lead 70. The lead contains wires electrically connecting electrodes 72 to stimulator 100. Stimulator 100 contains electrical components 12 that produce electrical stimulation pulses that travel through the wires of lead 70 and are delivered to electrodes 72, and thus to the tissue surrounding electrodes 72. To protect the electrical components inside stimulator 100, the case of the stimulator is preferably hermetically sealed, as discussed earlier. For additional protection against, e.g. impact, the case is preferably made of metal (e.g. titanium) or ceramic, which materials are also, advantageously, biocompatible. In addition, stimulator 100 is preferably Magnetic Resonance Imaging (MRI) compatible.

In the case of treatment alternatively or additionally constituting drug infusion, and as illustrated in FIG. 5, catheter(s) 80 are coupled at a proximal end to stimulator 100, which contains at least one pump 65 for storing and dispensing one or more drug(s) through the catheter(s) 80. At and/or along a distal end, catheter 80 has at least one discharge portion 82 for infusing dosages of the one or more drugs into a predetermined site in the brain tissue.

In one preferred embodiment, shown in FIG. 5, stimulator 100 includes a rechargeable battery as a power source/storage device 15. The battery is recharged, as required, from an external battery charging system (EBCS) 92, typically through an inductive link 94. In this embodiment, stimulator 100 includes a processor and other electronic circuitry 12 that allow it to generate electrical/infusion pulses that are applied to the patient through electrodes 72 and/or catheter(s) 80 in accordance with a program stored in programmable memory 18.

According to one preferred embodiment of the invention, such as depicted in FIG. 5, at least one lead 70 is attached to stimulator 100 via a suitable connector(s) 68, if necessary. Each lead includes at least two electrodes 72, and may include as many as sixteen or more electrodes 72. Additional leads 70' and/or catheter(s) 80' may be attached to stimulator 100. Hence, FIG. 5 shows (in phantom lines) a second catheter 80', and a second lead 70', having electrodes 72' thereon, also attached to stimulator 100.

Lead(s) 70 are preferably less than 5 mm in diameter, and more preferably less than 1.5 mm in diameter. Electrodes 72, 72' are preferably arranged as an array, more preferably are at least two collinear electrodes, and more preferably at least 4 collinear electrodes. Stimulator 100 is preferably programmable to produce either monopolar electrical stimulation, e.g., using the stimulator case as an indifferent electrode, or bipolar electrical stimulation, e.g., using one of the electrodes of the electrode array as an indifferent electrode. A preferred stimulator 100 has at least four channels and drives up to sixteen electrodes or more.

In one preferred embodiment, stimulator 100 of the present invention is activated and deactivated, programmed and tested through a hand held programmer (HHP) 101 (which may also be referred to as a patient programmer and is preferably, but not necessarily, hand held), a clinician programming system (CPS) 102 (which may also be hand held), or a manufacturing and diagnostic system (MDS) 103 (which may also be hand held). HHP 101 may be coupled to stimulator 100 via an RF link 95. Similarly, MDS 103 may be coupled to stimulator 100 via another RF link 96. In a like manner, CPS 102 may be coupled to HHP 101 via an infra-red link 97; and MDS 103 may be coupled to HHP 101 via another infra-red link 98. Other types of telecommunicative links, other than RF or infra-red may also be used for these purposes. Through these links, CPS 102, for example, may be coupled through HHP 101 to stimulator 100 for programming or diagnostic purposes. MDS 103 may also be coupled to stimulator 100, either directly through RF link 96, or indirectly through the IR link 98, HHP 101, and RF link 95.

For example, the electrical and/or drug stimulation can increase the activity of the pudendal afferents, thereby modulating the activity of the lower urinary tract via reflexive mechanisms and/or can increase the activity of the pudendal afferents, thereby acting to increase the tone of the urethral and/or anal sphincter. Such excitatory stimulation is likely to be produced by low-frequency electrical stimulation, an excitatory neurotransmitter agonist(s) (e.g., acetylcholine), an inhibitory neurotransmitter antagonist(s), a neural depolarizing agent, or any other drug that acts to cause a portion of an axon to generate an action potential.

Electrical stimulation parameters of, for instance, the pudendal nerve and other somatic nerves emanating from a sacral root will generally fall in the following ranges:

Frequency: 2–20 pulses per second (pps).
Duration: 50–350 microseconds ($\mu s$).
Amplitude: 1–5 volts at about 1–50 milliamps (mA).

It is to be understood that the above ranges are not absolute. Rather, they provide a guide for the stimulation parameters to be used. One of the attractive features provided by the invention is that the stimulation parameters are programmable and can be adjusted, as required, until an appropriate and efficacious stimulation regime is achieved.

Once again, stimulation and control parameters may be adjusted to levels that are safe and efficacious and cause the least discomfort, and parameters may also be chosen to target specific neural populations and to exclude others, or to increase neural activity in specific neural populations and to decrease neural activity in others. For example, relatively low frequency neurostimulation (i.e., less than about 50–100 Hz) typically has an excitatory effect on surrounding neural tissue, leading to increased neural activity, whereas relatively high frequency neurostimulation (i.e., greater than about 50–100 Hz) typically has an inhibitory effect, leading to decreased neural activity. Similarly, excitatory neurotransmitters (e.g., acetylcholine) agonists thereof, and agents that act to increase levels of an excitatory neurotransmitter(s) (e.g., edrophonium) generally have an excitatory effect on neural tissue, while inhibitory neurotransmitters (e.g., gamma-aminobutyric acid, a.k.a. GABA), generally have an inhibitory effect. However, antagonists of inhibitory neurotransmitters (e.g., bicuculline) and agents that act to decrease levels of an inhibitory neurotransmitter(s) have been demonstrated to excite neural tissue, leading to increased neural activity.

For example, somatic nerves that originate from S2, S3, and S4 nerve roots, e.g. the pudendal nerve and its nerve branches, may be stimulated to treat incontinence, urgency, frequency, and/or pelvic pain. In one alternative, exciting the urethral branch of the pudendal nerve will inhibit defecation in some patients. Low-frequency electrical stimulation (e.g., less than about 50–100 Hz) and/or infusion of, e.g., acetylcholine, is likely to produce such excitement. In another alternative, exciting other branches of the pudendal nerve, especially the dorsal nerve of the clitoris in the female and the dorsal nerve of the penis in the male, will prevent urination and/or defecation in some patients. Once again, low-frequency stimulation and/or infusion of, e.g., acetylcholine, is likely to provide this excitement.

In another alternative, exciting the pudendal nerve at the point where it passes through the pudendal canal (a.k.a. Alcock's Canal) will prevent urination and/or defecation and/or will control pelvic pain in some patients. Once again, low-frequency stimulation and/or infusion of, e.g., acetylcholine, is likely to provide this excitement.

As a further example, large diameter fibers (e.g., A-$\alpha$ and/or A-$\beta$ fibers) respond to relatively lower current density stimulation compared with small diameter fibers (e.g., A-$\delta$ and/or C fibers). Typically, relatively large diameter nerve fibers respond to pressure and light touch, while smaller fibers respond to pain. For example, stimulation of the pudendal nerve with relatively low current density may cause relatively non-painful (e.g., tingling) sensations that may treat incontinence in some patients.

Advantageously, by implanting one or more stimulators in the manner described herein so as to selectively stimulate appropriate nerves and/or tissue, it is possible to create a system which: (1) reduces or eliminates the incidence of unintentional episodes of bladder or colon emptying by stimulating nerve pathways that diminish involuntary bladder or colon contractions, (2) improves closure of the bladder/colon outlet, (3) improves the long-term health of the urinary system by increasing bladder capacity and period between emptying and/or (4) reduces or eliminates pelvic pain.

According to one embodiment of the invention, a stimulator operates independently. According to another embodiment of the invention, a stimulator operates in a coordinated manner with other stimulator(s), other implanted device(s), or other device(s) external to the patient's body. For instance, a stimulator may control or operate under the control of another implanted stimulator(s), other implanted device(s), or other device(s) external to the patient's body. A stimulator may communicate with other implanted stimulators, other implanted devices, and/or devices external to a patient's body via, e.g., an RF link, an ultrasonic link, or an optical link. Specifically, a stimulator may communicate with an external remote control (e.g., patient and/or physician programmer) that is capable of sending commands and/or data to a stimulator and that is preferably capable of receiving commands and/or data from a stimulator.

In order to help determine the strength and/or duration of electrical stimulation and/or the amount and/or type(s) of stimulating drug(s) required to produce the desired therapeutic effect, in one preferred embodiment, a patient's response to and/or need for treatment is sensed. For instance, the muscle activity produced in response to stimulation may be detected, e.g., via recording of the associated electromyograph (EMG). Thus, when electrodes and/or catheters of a stimulator are implanted, for example, near the dorsal nerve of the clitoris (a branch of the pudendal nerve), the signals from an EMG sensor built into the stimulator may be used to adjust stimulation parameters.

Alternatively, a "stimulator" dedicated to sensory processes communicates with a stimulator that provides the electrical and/or infusion pulses. For instance, a "microstimulator" may be introduced into the bladder to sense changes in bladder pressure. As described below, the implant circuitry 12 may, if necessary, amplify and transmit these signals, which may be analog or digital. Other methods of determining the required stimulation include sensing bladder volume, impedance, absorption of light, sphincter or colon pressure, muscular activity associated with the sphincter, bladder, or colon via electromyograph, observing the stimulation required to decrease or eliminate pain, sensing other measures of the state of the patient, such as levels or changes of any blood borne substance, including medications and hormones, and other methods mentioned herein, and others that will be evident to those of skill in the art upon review of the present disclosure. The sensed information is preferably used to control the stimulation parameters in a closed-loop manner.

Figure 7:
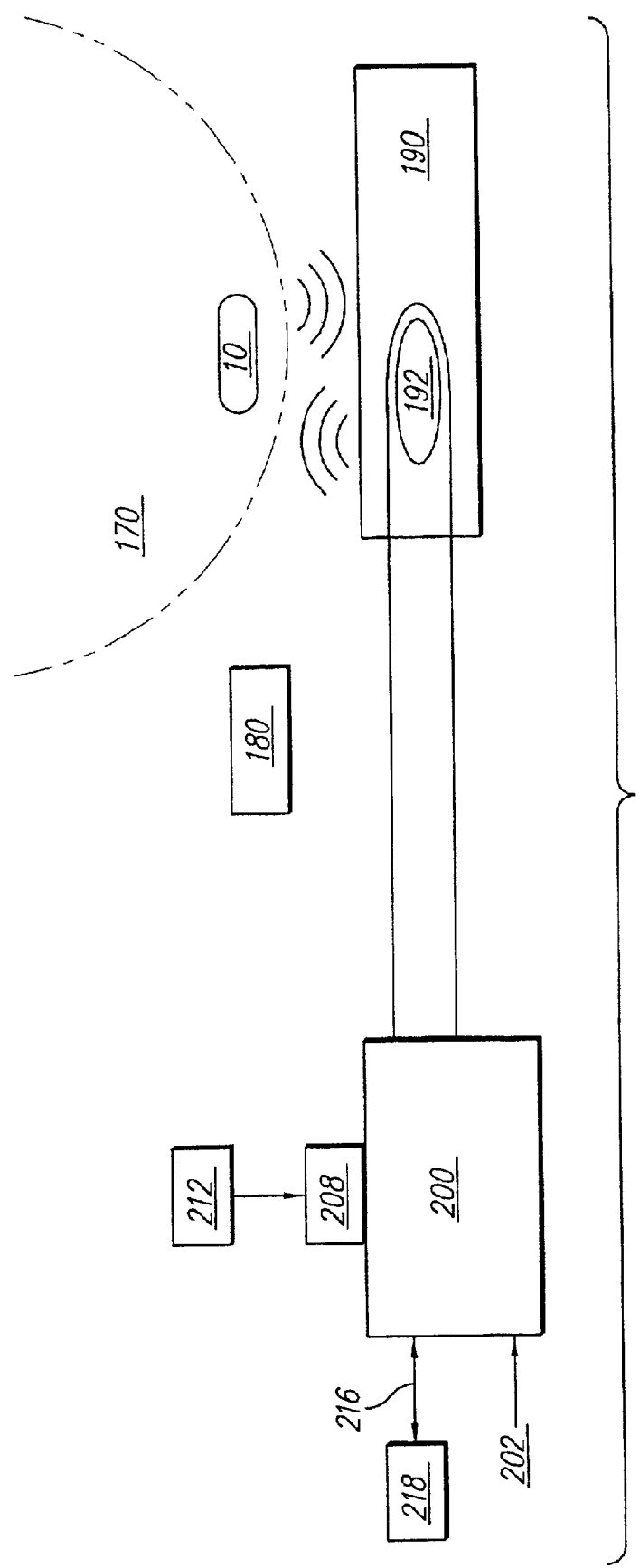
FIG. 7 illustrates an additional exemplary embodiment of external components of the invention.

In another preferred embodiment as illustrated in FIG. 7, using for example, a microstimulator(s), the patient 170 switches implantable microstimulator 10 on and off by use of controller 180, which is preferably handheld. Controller 180 operates to control implantable stimulator 10 by any of various means, including sensing the proximity of a permanent magnet located in controller 180, or sensing RF transmissions from controller 180.

External components for one preferred embodiment related to programming and providing power to stimulator 10 are also illustrated in FIG. 7. When it is required to communicate with implanted stimulator 10, patient 170 is positioned on or near external appliance 190, which appliance contains one or more inductive coils 192 or other means of communication (e.g., RF transmitter and receiver). External appliance 190 is connected to or is a part of external electronic circuitry appliance 200 which receives power 202 from a conventional power source. External appliance 200 contains manual input means 208, e.g., a keypad, whereby the patient 170 or a caregiver 212 may request changes in the parameters of the electrical and/or drug stimulation produced during normal operation of implantable stimulator 10. In this embodiment, manual input means 208 includes various electromechanical switches and visual display devices that provide the patient and/or caregiver with information about the status and prior programming of implantable stimulator 10.

Alternatively or additionally, external electronic appliance 200 is preferably provided with an electronic interface means 216 for interacting with other computing means 218, such as by a serial interface cable or infrared link to a personal computer or to a telephone modem. Such interface means 216 thus permits a clinician to monitor the status of the implant(s) and prescribe new stimulation parameters from a remote location.

The external appliance(s) may advantageously be embedded in a cushion, mattress cover, or garment. Other possibilities exist, including a belt, strap, or other structure that may be affixed to the patient's body or clothing.

Thus, it is seen that in accordance with the present invention, one or more external appliances are preferably provided to interact with the stimulator(s) to accomplish one or more of the following functions:

Function 1: If necessary, transmit electrical power from the external electronic appliance 200 via appliance 190 to stimulator 10 in order to power the device and/or recharge the power source/storage device 15. External electronic appliance 200 may include an automatic algorithm that adjusts electrical and/or stimulation parameters automatically whenever the stimulator(s) 10 is/are recharged.

Function 2: Transmit data from the external appliance 200 via the external appliance 190 to stimulator 10 in order to change the parameters of electrical and/or drug stimulation produced by stimulator 10.

Function 3: Transmit sensed data indicating a need for treatment or in response to stimulation (e.g., pressure, neural activity (e.g., ENG), muscle activity (e.g., EMG), impedance, or other activity) to external appliance 200 via external appliance 190.

Function 4: Transmit data indicating state of the stimulator (e.g., battery level, drug level, electrical stimulation an/or infusion settings, etc.) to external appliance 200 via external appliance 190.

By way of example, a treatment modality for incontinence may be carried out according to the following sequence of procedures:

1. A first stimulator 10 is implanted so that its electrodes 14 and 16 are located adjacent to nerve fibers 8. A second stimulator 10 is implanted into the bladder.

2. Using Function 2 described above (i.e., transmitting data) of external electronic appliance 200 and external appliance 190, the first implantable stimulator 10 is commanded to produce a series of excitatory electrical stimulation pulses with gradually increasing amplitude, possibly while infusing gradually increasing amounts of an excitatory neurotransmitter, e.g., acetylcholine.

3. After each stimulation/infusion pulse, or at some other predefined interval, any change in bladder pressure resulting from the electrical an/or drug stimulation is sensed by the second implantable stimulator 10. These responses are converted to data and telemetered out to the external electronic appliance 200 via Function 3.

4. From the response data received at external appliance 200 from the second implantable stimulator 10, the stimulus threshold for obtaining a reflex response is determined and is used by a clinician acting directly 212 or by other computing means 218 to transmit the desired electrical and/or drug stimulation parameters to the first implantable stimulator 10 in accordance with Function 2.

5. When patient 170 desires to invoke electrical stimulation and/or drug infusion, patient 170 employs controller 180 to set the first stimulator 10 in a state where it delivers a prescribed stimulation pattern from a predetermined range of allowable stimulation patterns.

6. Patient 170 employs handheld controller 180 to turn off the first stimulator 10, if desired.

7. Periodically, the patient or caregiver recharges the power source/storage device 15 of the first and/or second implantable stimulator 10, if necessary, in accordance with Function 1 described above (i.e., transmit electrical power).

In another example, referring again to FIG. 5, a treatment modality for incontinence may be carried out according to the following sequence of procedures:

1. A stimulator 100 is implanted in the inner thigh, buttocks, abdomen, flank, or other remote location, and its lead 70 and/or catheter 80 tunneled so that electrodes 72 and/or catheter discharge portion 82 are located adjacent to the pudendal nerve 164 at Alcock's canal 167 (FIG. 6C). If necessary or desired, additional leads 70' and/or catheters 80' may be used so that additional electrodes 72' and/or catheter discharge portions(s) 82' may additionally or alternatively be located in or adjacent sacral nerve roots. Additional electrodes 72' may be implanted, e.g., on the bladder.
2. Using HHP 101 described above, stimulator 100 is commanded to produce a series of excitatory electrical stimulation pulses with gradually increasing amplitude, possibly while infusing gradually increasing amounts of an excitatory neurotransmitter, e.g., acetylcholine.
3. After each stimulation/infusion pulse, or at some other predefined interval, any change in bladder pressure resulting from the electrical an/or drug stimulation is sensed by the additional electrodes 72' implanted on the bladder.
4. These responses are converted to data and telemetered out to HHP 101, and from there, to CPS 102. From the response data received at CPS 102, the stimulus threshold for obtaining a reflex response is determined and is used by a clinician using CPS 102 and/or HHP 101 to transmit the desired electrical and/or drug stimulation parameters to stimulator 100. Alternatively, the response data are converted to data and used directly by stimulator 100 to modify electrical and/or drug stimulation parameters in a closed-loop method.
5. When patient 170 desires to invoke electrical stimulation and/or drug infusion, patient 170 employs HHP 101 to set stimulator 100 in a state where it delivers a prescribed stimulation pattern from a predetermined range of allowable stimulation patterns.
6. Patient 170 employs HHP 101 to turn off stimulator 100, if desired.
7. Periodically, the patient or caregiver recharges the power source/storage device 15 of the stimulator 100, if necessary, using EBCS 92.

For the treatment of any of the various types and severities of incontinence, urgency, frequency, or pelvic pain, it may be desirable to modify or adjust the algorithmic functions performed by the implanted and/or external components, as well as the surgical approaches, in ways that would be obvious to skilled practitioners of these arts. For example, it may be desirable to employ more than one implantable stimulator 10, each of which could be separately controlled by means of a digital address. Multiple channels and/or multiple patterns of electrical and/or drug stimulation might thereby be programmed by the clinician and controlled by the patient in order to deal with complex or multiple symptoms or dysfunctions such as may occur as a result of spinal cord injury and neurodegenerative disorders.

In one preferred embodiment, a stimulator, or a group of two or more stimulators, is controlled via closed-loop operation. A need for and/or response to stimulation is sensed by the stimulator(s), or by an additional "stimulator" (which may or may not be dedicated to the sensing function), or another implanted or external device.

If necessary, the sensed information is transmitted to the stimulating stimulator(s). Preferably, the parameters used by the stimulator(s) are automatically adjusted based on the sensed information. Thus, the electrical and/or drug stimulation parameters are adjusted in a closed-loop manner to provide stimulation tailored to the need for and/or response to the electrical and/or drug stimulation.

For instance, in one embodiment of the present invention, a first and second "stimulator" are provided. The second "stimulator" periodically (e.g. once per minute) records bladder pressure and transmits it to the first stimulator. The first stimulator uses the bladder pressure information to adjust electrical and/or drug stimulation parameters according to an algorithm programmed, e.g., by a physician. For example, the amplitude of electrical stimulation may be increased in response to increased bladder pressure. More preferably, one stimulator performs both the sensing and stimulating functions.

While a stimulator may also incorporate means of sensing incontinence, urgency, frequency, or pain, e.g., via a pressure sensor or electromyograph, it may alternatively or additionally be desirable to use a separate or specialized implantable device to record and telemeter physiological conditions/responses in order to adjust electrical stimulation and/or drug infusion parameters. This information may be transmitted to an external device, such as external appliance 190, or may be transmitted directly to implanted stimulator(s). However, in some cases, it may not be necessary or desirable to include a sensing function or device, in which case stimulation/infusion parameters are determined and refined, for instance, by patient feedback.

While the invention herein disclosed has been described by means of specific embodiments and applications thereof, numerous modifications and variations could be made thereto by those skilled in the art without departing from the scope of the invention set forth in the claims.

What is claimed is:

1. A method of treating patients, comprising:
   providing a stimulator that generates a stimulation pulse in accordance with prescribed stimulation parameters;
   providing at least one of
   a) a lead connected to the stimulator, which lead includes at least two electrodes and
   b) a catheter connected to the stimulator, which catheter includes a discharge portion
   wherein the stimulation pulse is delivered to a pudendal nerve at adjacent the electrodes or catheter discharge portion;
   perineally or vaginally implanting the electrodes and/or catheter discharge portion adjacent to the pudendal nerve to be stimulated;
   implanting the stimulator at a location remote from the pudendal nerve to be stimulated; and
   tunneling the lead and/or catheter subcutaneously to the stimulator location.

2. The method of claim 1 wherein the pudendal nerve to be stimulated includes at least one branch of at least one pudendel nerve.

3. The method of claim 2 wherein the stimulation is delivered at less than about 50 to 100 Hz.

4. The method of claim 1 wherein the at least one implantable stimulator further comprises at least one sensor.

5. The method of claim 4 further comprising sensing a condition using the at least one sensor and adjusting the stimulation parameters based on the sensed condition.

6. The method of claim 5 further comprising performing the parameter adjustment using at least one external appliance.

7. The method of claim 5 further comprising performing the parameter adjustment using the implantable stimulator.

8. A method for stimulating at least one tissue affecting specific anatomical structures of the perineum, comprising:
proviging a stimulator that generates a stimulation pulse in accordance with prescribed stimulation parameters;
providing at least one of
a) a lead connected to the stimulator, which lead included at least two electrodes and
b) a catheter connected to the stimulator, which catheter includes at least one discharge portion,
wherein the stimulation pulse is delivered to a pudendal nerve adjacent the electrodes or catheter discharge portion;
implanting the electrodes and/or catheter discharge portion adjacent to the pudendal nerve of the perineum to be stimulated;
implanting the stimulator at a location remote from the pudendal nerve to be stimulated; and
tunneling the lead and/or catheter subcutaneously to the stimulator location.

9. The method of claim 8 wherein implanting the electrodes and/or catheter discharge portion is executed with a perineal approach, which perineal approach includes steps for guiding an insertion tool through the skin of the perineum and depositing the electrodes and/or catheter discharge portion adjacent to the pudendal nerve to be stimulated.

10. The method of claim 9 further comprising providing a programmable memory within the stimulator for receiving and retaining the stimulation parameters.

11. The method of claim 9 further comprising providing a power source within the stimulator for providing operating power to the stimulator.

12. The method of claim 9 further comprising providing at least one external appliance for transmitting the stimulation parameters to the stimulator.

13. The method of claim 9 further comprising providing at least one sensor to sense a physical condition, and adjusting the stimulation parameters based on the sensed condition.

14. The method of claim 9 further comprising adjusting the stimulation parameters using at least one external appliance.

15. The method of claim 9 further comprising adjusting the stimulation parameters using the implantable stimulator.

16. The method of claim 9 wherein the stimulator is configured to generate an electrical stimulation pulse.

17. The method of claim 9 wherein the stimulation is configured to generate a drug infusion stimulation pulse.

18. A method of treating a patient, comprising:
providing at least one stimulator that generates at least one stimulation pulse in accordance with prescribed stimulation parameters of a stimulation regime;
providing at least one lead, which lead includes at least one electrode;
electrically connecting the at least one lead to the at least one stimulator;
delivering the at least one stimulation pulse to a portion of at least one pudendal nerve adjacent the at least one electrode;
implanting the at least one lead wherein the at least one electrode is implanted adjacent to the at least one pudendal nerve; and
implanting the at least one stimulator at a location remote from the at least one pudendal nerve to be stimulated; and
wherein at least a branch of the at least one pudendal nerve leads to the perineum of a patient.

19. The method of claim 18 wherein the at least one stimulator is at least one implantable pulse generator.

20. The method of claim 19 further comprising providing operating power to the at least implantable pulse generator from a rechargeable power source.

21. The method of claim 19 further comprising:
providing operating power to the at least one implantable pulse generator; and
transmitting stimulation parameters to the at least one implantable pulse generator from at least one external appliance.

* * * * *